(12) United States Patent
Chiba et al.

(10) Patent No.: US 7,507,587 B2
(45) Date of Patent: Mar. 24, 2009

(54) AUTOMATIC ANALYSIS AND CONTROL SYSTEM FOR ELECTROLESS COMPOSITE PLATING SOLUTION

(75) Inventors: Tadashi Chiba, Hirakata (JP); Koji Monden, Nagoya (JP); Kazuki Yoshikawa, Hirakata (JP); Shinji Tachibana, Hirakata (JP)

(73) Assignee: C.Uyemura Co., Ltd., Osaka (JP)

( * ) Notice: Subject to any disclaimer, the term of this patent is extended or adjusted under 35 U.S.C. 154(b) by 154 days.

(21) Appl. No.: 11/287,285

(22) Filed: Nov. 28, 2005

(65) Prior Publication Data

US 2006/0078465 A1    Apr. 13, 2006

Related U.S. Application Data

(63) Continuation of application No. 10/031,461, filed as application No. PCT/JP01/04222 on May 21, 2001, now abandoned.

(51) Int. Cl.
*G01N 21/00* (2006.01)
*G01N 21/62* (2006.01)

(52) U.S. Cl. .......................... 436/164; 436/171; 436/172

(58) Field of Classification Search .................. None
See application file for complete search history.

(56) References Cited

U.S. PATENT DOCUMENTS 1,953,329 A * 4/1934 Altenkirch .................... 62/85
4,406,248 A * 9/1983 Araki et al. .................. 118/690
4,774,101 A * 9/1988 Harris et al. .................... 427/8

FOREIGN PATENT DOCUMENTS

| JP | 48-060694 A | | 8/1973 |
| JP | 48-100181 A | | 12/1973 |
| JP | 55023433 A | * | 2/1980 |
| JP | 02-020149 A | | 1/1990 |
| JP | 03-104856 A | | 5/1991 |
| JP | 10142143 A | * | 5/1998 |
| JP | 10142144 A | * | 5/1998 |

* cited by examiner

*Primary Examiner*—Yelena G Gakh
(74) *Attorney, Agent, or Firm*—Sughrue Mion, PLLC

(57) ABSTRACT

An automatic analysis and control system for electroless composite plating solution for automatically analyzing an electroless composite plating solution and performing such a control as to obtain an appropriate bath composition and/or use conditions, wherein, as a technique for measuring the concentration of a metallic component in the plating solution by absorptiometry, the system includes a mechanism for measuring transmissivity or absorbance at least two or more different wavelengths after the plating solution is automatically introduced into an analytical cell, and a mechanism for calculating the objective concentration from the measured values and displaying the calculation results.

7 Claims, 15 Drawing Sheets

US 7,507,587 B2

AUTOMATIC ANALYSIS AND CONTROL SYSTEM FOR ELECTROLESS COMPOSITE PLATING SOLUTION

This is a continuation of application Ser. No. 10/031,461 filed Jan. 22, 2002 now abandoned, The entire disclosure(s) of the prior application(s), application Ser. No. 10/031,461 is hereby incorporated by reference.

This application is the national phase under 35 U.S.C. §371 of PCT International Application No. PCT/JP01/04222 which has an International filing date of May 21, 2001 which designated the United States of America, the entire contents of which are hereby incorporated by reference.

TECHNICAL FIELD

The present invention relates to an automatic analysis and control system for an electroless composite plating solution.

BACKGROUND ART

Request for quality of platings has become higher in recent years, and appropriate control of plating solutions has become much burden on the production sites. On the other hand, as an element of endeavor for cost-down coping with competition in price, automation of plating treatments has been progressing, and, as a result, an automatic control system for plating solutions has come to be indispensable.

Particularly, in the industry of plating in recent years, demand for electroless plating, particularly electroless nickel plating is very large, and such plating is used widely. As compared with electroplating, the electroless plating requires a very high frequency of analysis and an extremely high frequency of material replenishment, so that liquid control systems combining automatic analysis and automatic material replenishment have been developed and put to practical use over years. The liquid control systems have been widely adopted as an important element of electroless plating equipment.

Details of the above-mentioned systems are explained in literature such as "Automatic Control of Plating Bath", Hyomen Gijutsu (Surface Technology), Vol. 34, No. 6, 1983, and "Automatic Control of Electroless Plating Bath", Jitsumu Hyomen Gijutsu (Practical Surface Technology), Vol. 31, No. 10, 1984.

While a plating solution contains various components, the components analyzed by an automatic liquid control system are very limited components such as, for example, a component used as a standard for replenishment or a component most important for securing plating quality, and there is substantially no case where all components are analyzed.

Where there is a component which is not analyzed by the automatic liquid control system but must be periodically analyzed, manual analysis is carried out, and a control is conducted, if required. In practice, however, most components are substantially not analyzed or controlled.

In concrete, in the automatic liquid control system for electroless nickel plating solution, the components analyzed are usually Ni concentration and pH. Particularly, in electroless nickel plating, control of the Ni concentration is the most important. Since the Ni concentration is gradually lowered due to consumption of the Ni component when electroless nickel plating is carried out, the Ni component is sequentially replenished for maintaining the Ni concentration at a predetermined value. It is general liquid control means to replenish other components also, in proportional manner, with the amount of the Ni component replenished as a measure. In other words, the Ni concentration is utilized as a standard for ideal control of all the components, so that the accuracy of analysis of the Ni concentration in the liquid control is very important.

As an analyzing method for Ni concentration, chelatometric titration and absorptiometry are general ones, and, at present, the absorptiometry is generally used in an automatic liquid control system for the electroless nickel plating. The absorptiometry has a very long history as one means of analyzing composition by instrumental analysis, and includes various techniques from colorimetry in which concentration is measured through comparison of solution colors to spectrophotometry in which absorbance is measured by use of light with a wavelength in an extremely narrow range close to monochromatic light. The principles and analyzing techniques of absorptiometry are described in detail in "Instrumental Analysis Guide Book" (edited by the corporate juridical person the Analytical Chemical Society of Japan, published by Maruzen Co., Ltd. Jul. 10, 1996), and "Experiments and Computation in Quantitative Analysis" (written by Seiji Takagi, published by Kyoritsu Syuppan Co., Ltd., first published on Nov. 5, 1961). In actual quantitative analysis of the Ni concentration in an electroless nickel plating solution by absorptiometry, absorbency of light with a wavelength in green color portion in the visible region is measured.

The electroless nickel plating solution contains various complexing agents, the Ni component is present as an Ni complex ion, which strongly absorbs light in the wavelength region of green color, and there is a good proportionality relationship between the absorbance in the wavelength region and the Ni concentration. By utilizing this characteristic feature, quantitative analysis with high accuracy is performed. To perform measurement in a specified wavelength region, the light must be spectrometrically conditioned, so that most systems for analysis adopt the technique of selecting light by interference filter. Alternatively, there is a method in which a wavelength extremely close to monochromatic light is obtained by monochrometer using a diffraction grating or a prism. However, this method is rarely used because of complicated mechanism and comparatively high cost, and because such a high spectrometric treatment is not needed for analytical accuracy of Ni concentration required in the conventional liquid control systems.

Not limited to electroless plating, there are many cases where the absorptiometry is used as an automatic liquid control system or liquid analysis method, and many patent applications are found on patent investigations.

However, there is found almost no proposal as to the measuring method in an automatic liquid control system for an electroless composite plating solution.

As mentioned above, although automatic liquid control systems for electroless plating solution have been put to practical use and widely spread, use of the existing liquid control system for the purpose of controlling an electroless composite plating leads to various problems. First, in the case of an electroless nickel plating solution, many of the existing systems use absorptiometry as the method of measuring Ni concentration. In that case, the wavelength of the light for measurement is the wavelength at which the absorption of light due to Ni complex is present. In many cases, the measurement is conducted at one wavelength in the visible region (VIS; wavelength range from 400 to 750 nm).

In the case of measuring a composite plating solution, however, the incident light is not only transmitted straight and absorbed but also reflected, diffracted or scattered by the suspended particles. The light reflected, diffracted or scattered by the suspended particles leads to apparent decrease of the transmitted light, and cannot be distinguished from the decrease of the transmitted light due to absorption by the objective component, resulting in that the amount of the objective component is erroneously judged to be more than the real amount. In addition, the degree of influence of the suspended particles varies depending on the kind, particle size distribution and concentration of the suspended particles, and depending on various factors of the plating solution. For example, when the plating solution is specified, the influence of the suspended particles is comparatively stabilized, so that the concentration of the objective component can be measured with comparatively good accuracy by preliminarily deeming a fixed value as the decrease of transmissivity due to turbidity. However, the electroless plating solution shows a large variation in composition as it is used, and influences of the variation must be corrected, so that the method of allowing for the influence of turbidity by use of a fixed value is limited in practicality.

In addition, when a special trouble is generated, for example, when special foreign particulates are taken into the plating solution and bad dispersion is generated, the turbidity is greatly changed, resulting in large errors in the analytical results of the objective component. Besides, also when a plating solution sampling mechanism is out of order so that a plating solution with uniform dispersion of particulates cannot be sampled, there is a fear that gravy and fatal analytical errors would be generated.

Thus, it can be said that it is substantially impossible to secure the required accuracy and reliability by simply using the analytical method in the conventional systems. Although there are some countermeasures against the problems in the analysis of an electroless composite plating solution, the countermeasures have respective drawbacks.

For example, the method of measuring after separating the particulates dispersed in the plating solution by filtration, sedimentation, centrifugal separation or the like is accompanied by difficulties or cost demerit as to the mechanism for continuously or intermittently performing the separation, and liquid conditioning is very difficult since the plating solution is wasted attendant on the analysis. On the other hand, the method of analyzing by chelatometric titration is attended by high complicatedness of system, and requires a sampling device with very high precision and reliability for securing accuracy. In addition, a large amount of waste liquid is generated by analysis, and there is need for expendable chemicals for analysis such as an indicator and a titration liquid; thus, the chelatometric titration method has many minus factors, as compared with the absorptiometry.

It can be said that an ideal method is to perform measurement while keeping the plating solution as it is and return the plating solution into the plating tank in a recirculating cycle manner, without processing the plating solution for analysis or wasting the plating solution as in the general automatic analysis and control system for electroless plating solution according to the prior art.

DISCLOSURE OF THE INVENTION

It is an object of the present invention to provide an automatic analysis and control system for electroless composite plating solution, in a technique of analyzing an electroless composite plating solution, particularly analyzing the Ni concentration in an electroless composite nickel plating solution, by which it is possible to solve the problem of lowering of analytical accuracy due to the presence of suspended particles represented by fluroresins (PTFE, FEP, PFA, TFE oligomer and the like), graphite fluoride ($CF_x$), graphite, alumina ($Al_2O_3$), silicon carbide (SiC), boron nitride (BN) and the like, and it is possible to secure an analytical accuracy sufficient for practical use, and which is inexpensive.

In order to attain the above object, the present invention provides various contrivances on the basis of analytical method and system for securing a required analytical accuracy, in an automatic analysis and control system for automatically analyzing an electroless composite plating solution including particulates of graphite fluoride, graphite, alumina, silicon carbide, boron nitride or the like dispersed in an electroless plating solution, and automatically performing replenishment and liquid conditioning based on the analytical results. As mentioned above, the primary cause of troubles in quantitatively analyzing the concentration of a deposited metallic ion in an electroless composite plating solution by absorptiometry is the turbidity due to the particulates dispersed in the plating solution for co-deposition. It has been found out, by the studies of a method for solving the above problems, that the objective deposited metallic ion concentration can be obtained with a required accuracy by measuring absorbance at least two or more characteristic measurement wavelengths and performing an arithmetic operation on the measured values by related equations. Further, it has also been found out that various problems leading to generation of measurement errors are generated in the process of building up an automatic analysis and control system based on this method, but the problems can be solved by making contrivances as to the characteristic plating solution sampling mechanism, measurement conditions, operating conditions of the system and the like. Based on the findings, the present invention has been completed.

Accordingly, the present invention provides an automatic analysis and control system for electroless composite plating solution as follows.

(1) An automatic analysis and control system for electroless composite plating solution for automatically analyzing an electroless composite plating solution and performing such a control as to obtain an appropriate bath composition and/or use conditions, wherein, as a technique for measuring the concentration of a metallic component in the plating solution by absorptiometry, the system includes a mechanism for measuring transmissivity or absorbance at least two or more different wavelengths after the plating solution is automatically introduced into an analytical cell, and a mechanism for calculating the objective concentration from the measured values and displaying the calculation results.

(2) An automatic analysis and control system according to (1) above, wherein at least one of the measurement wavelengths is spectrometrically conditioned so that the half-width is 1 to not more than 100 nm.

(3) An automatic analysis and control system according to (1) or (2) above, wherein the combination of the measurement wavelengths is obtained by selecting at least one measurement wavelength in a wavelength range of 250 to 350 nm or 450 to 550 nm, and selecting at least one other measurement wavelength not overlapping with the at least one measurement wavelength in a wavelength range of 350 to 450 nm or 550 to 800 nm.

(4) An automatic analysis and control system according to (1), (2) or (3) above, wherein a measuring time table is so set that a standing time of not less than 15 sec is secured after the automatic introduction of the plating solution into the analytical cell and before the start of measurement of the transmissivity or absorbance.

(5) An automatic analysis and control system according to any one of (1) to (4) above, wherein a function of periodically introducing pure water into the analytical cell to wash the analytical cell and measuring the transmissivity or absorbance at a set measurement wavelength in the condition where the cell is filled with pure water is provided, and the thus measured value is used as a reference value of 100% transmissivity or zero absorbance relative to measured value of transmissivity or absorbance of the plating solution measured in the period before the next similar measurement for pure water.

(6) An automatic analysis and control system according to any one of (1) to (5) above, wherein a vertically elongate plating solution dwell portion having a cross sectional area of not less than two times of the cross sectional area of a sampling pipe is provided in the course of a sampling passage for introducing the plating solution into the analytical cell, an inlet to the plating solution dwell portion is provided at an upper portion, and an outlet from the plating solution dwell portion is provided at a lower portion, whereby a trap mechanism for preventing fine bubbles in the plating solution from being fed into the analytical cell is provided.

(7) An automatic analysis and control system according to any one of (1) to (6) above, wherein the electroless composite plating solution is an electroless composite nickel plating solution, and the nickel component in the plating solution is measured.

BEST MODE FOR CARRYING OUT THE INVENTION

Figure 1:
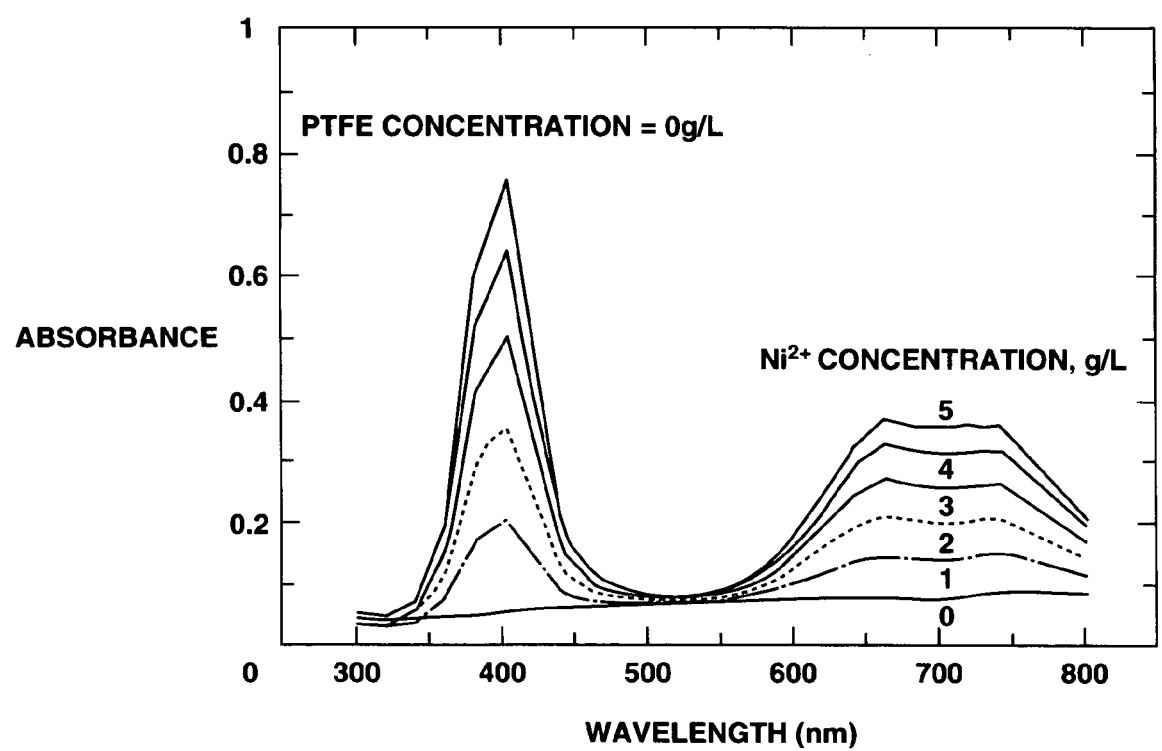
FIG. 1 is a graph showing the relationship between measurement wavelength and absorbance in the case where Ni concentration is varied in the range of 0 to 5 g/L, in an electroless nickel plating solution not containing PTFE.

The automatic analysis and control system for electroless composite plating solution according to the present invention comprises, as a technique of measuring the concentration of a metallic component in the plating solution by absorptiometry, a mechanism for automatically introducing the plating solution into an analytical cell and measuring transmissivity or absorbance at least two different wavelengths, and a mechanism for calculating the objective concentration from the measured values by an arithmetic operation and displaying the results of calculation.

Here, the electroless composite plating solution as the object of the present invention is one prepared by dispersing water-insoluble composite material particles in an electroless plating solution. As the electroless plating solution, there may be mentioned an electroless nickel plating solution, electroless nickel-cobalt plating solution, electroless cobalt plating solution, electroless copper plating solution and the like, using sodium hypophosphite, a boron-based reducing agent such as dimethylamineboran or the like as a reducing agent. As the composite material, there may be mentioned fluororesins (PTFE, FEP, PFA, TFE oligomer and the like), graphite fluoride ($CF_x$), graphite, alumina ($Al_2O_3$), silicon carbide (SiC), boron nitride (BN) and the like. As such an electroless composite plating solution, those of known bath compositions and commercially available baths may be used.

In this case, particularly, the present invention can be preferably adopted for measurement of nickel component in an electroless composite nickel plating solution. Here, the composition of the electroless composite nickel plating solution is not limited, and a preferable example is one in which Ni ion concentration is 1 to 10 g/L, particularly 3 to 7 g/L, and the concentration of the composite material particles of fluororesin or the like is not more than 30 g/L, particularly not more than 10 g/L. The lower limit of the content of the composite material particles is not particularly limited, and may be generally not less than 0.5 g/L, particularly not less than 1 g/L. The reducing agent is preferably a hypophosphite such as sodium hypophosphite, and the concentration thereof is 5 to 50 g/L, particularly 10 to 30 g/L. The method of the present invention is effectively adopted for an electroless composite nickel plating solution in which a phosphite such as sodium phosphite formed by oxidation of the hypophosphite attendant on the progress of plating is accumulated in a wide range of 0 to 300 g/L, particularly 0 to 200 g/L. The pH of the electroless composite nickel plating solution is generally 3 to 9, particularly 4 to 8.

In the present invention, transmissivity or absorbance is measured at least two different wavelengths, in analyzing a metallic component in the electroless composite plating solution, for example, the Ni component in the case of an electroless composite nickel plating solution. Namely, in the case of the electroless composite nickel plating solution, a method of combining the measurement of absorbance at a wavelength for measurement of Ni concentration (for example, 660 nm) and the measurement of absorbance at a wavelength in a specified range in a shorter wavelength region (for example, 520 nm) is adopted.

Now, the method of measurement at least two wavelengths and the effects thereof will be described while taking as a representative example an electroless composite nickel plating solution (electroless Ni—P/PTFE composite plating solution) containing sodium hypophosphite as a reducing agent and polytetrafluoroethylene (PTFE) particles as composite material particles.

Figure 2:
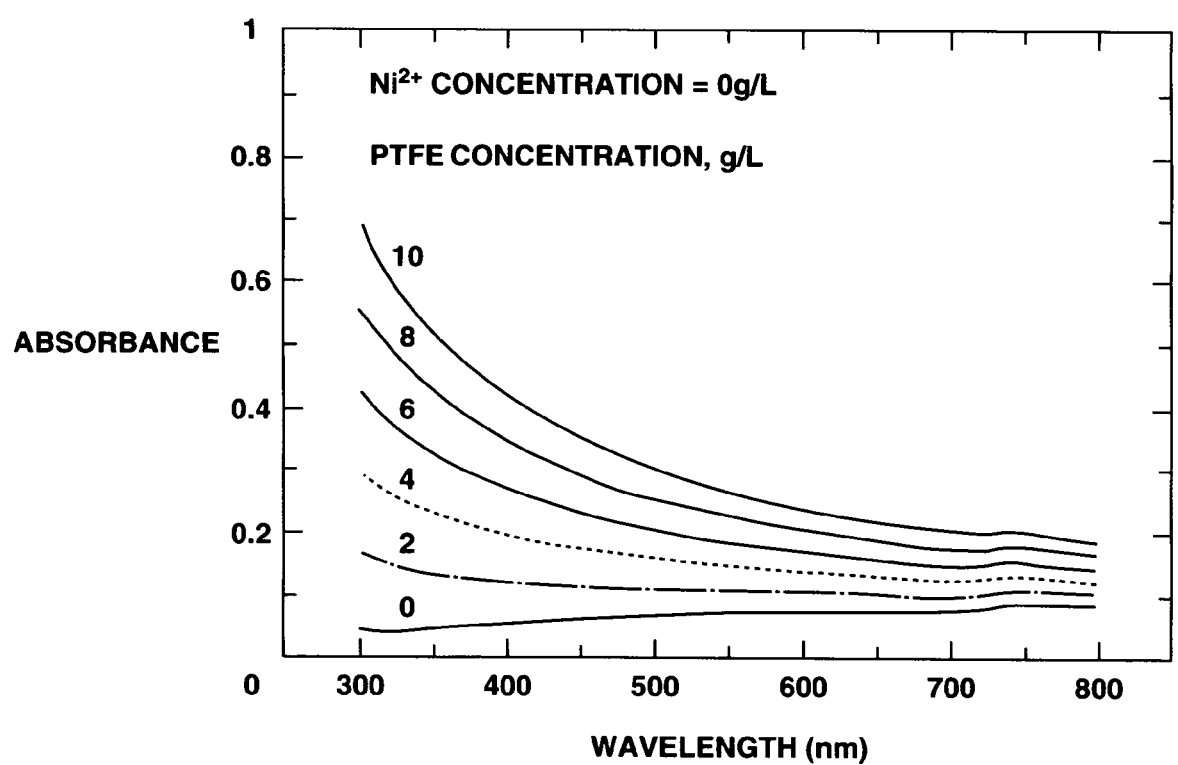
FIG. 2 is a graph showing the relationship between measurement wavelength and absorbance in the case where PTFE concentration is varied in the range of 0 to 10 g/L, in an electroless plating solution (Ni concentration: 0 g/L) containing PTFE as composite material particles and not containing metallic component.
Figure 3:
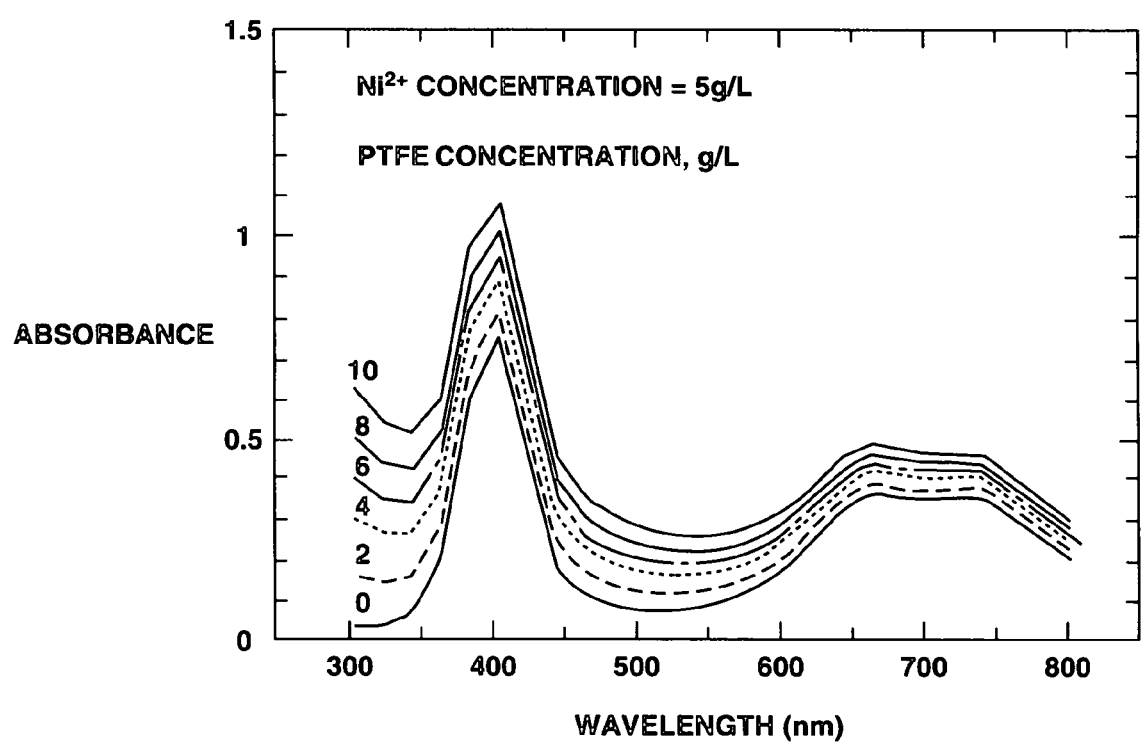
FIG. 3 is a graph showing the relationship between measurement wavelength and absorbance in the case where PTFE concentration is varied in the range of 0 to 10 g/L while Ni concentration is kept constant at 5 g/L, in an electroless composite nickel plating solution containing PTFE as composite material particles.
Figure 4:
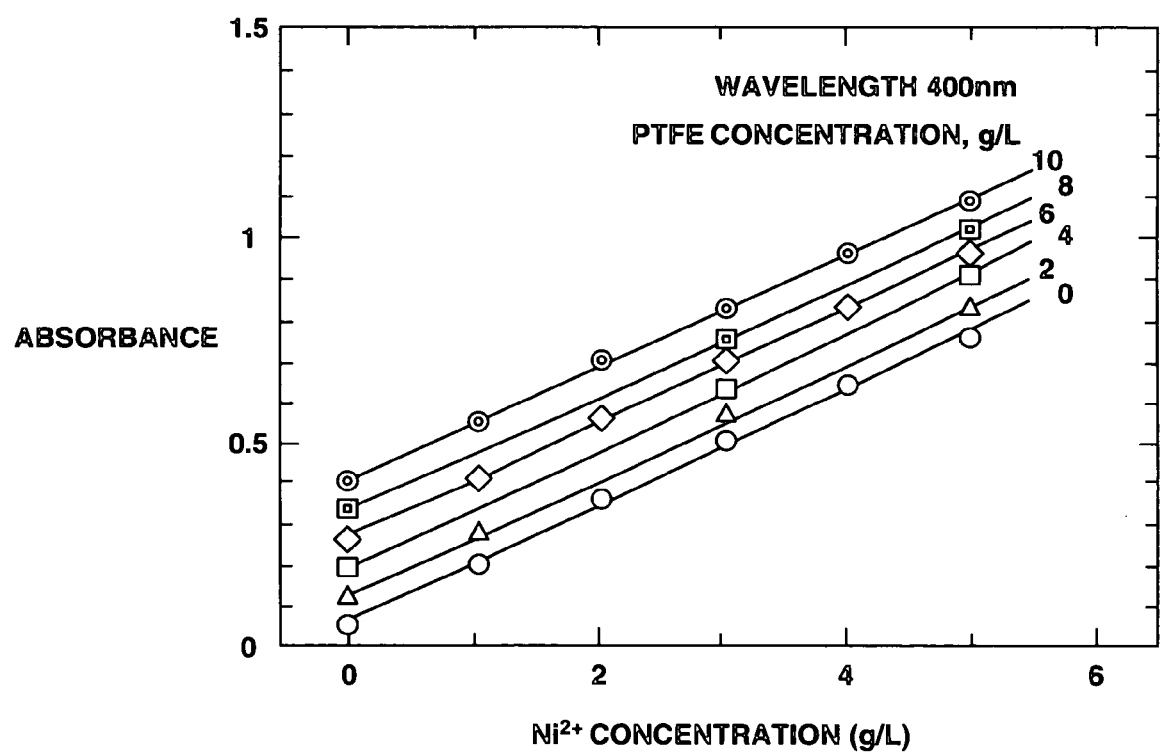
FIG. 4 is a graph showing the relationship between Ni concentration and absorbance at a wavelength of 400 nm in the case where PTFE concentration is varied in the range of 0 to 10 g/L, in an electroless composite nickel plating solution containing PTFE as composite material particles.
Figure 5:
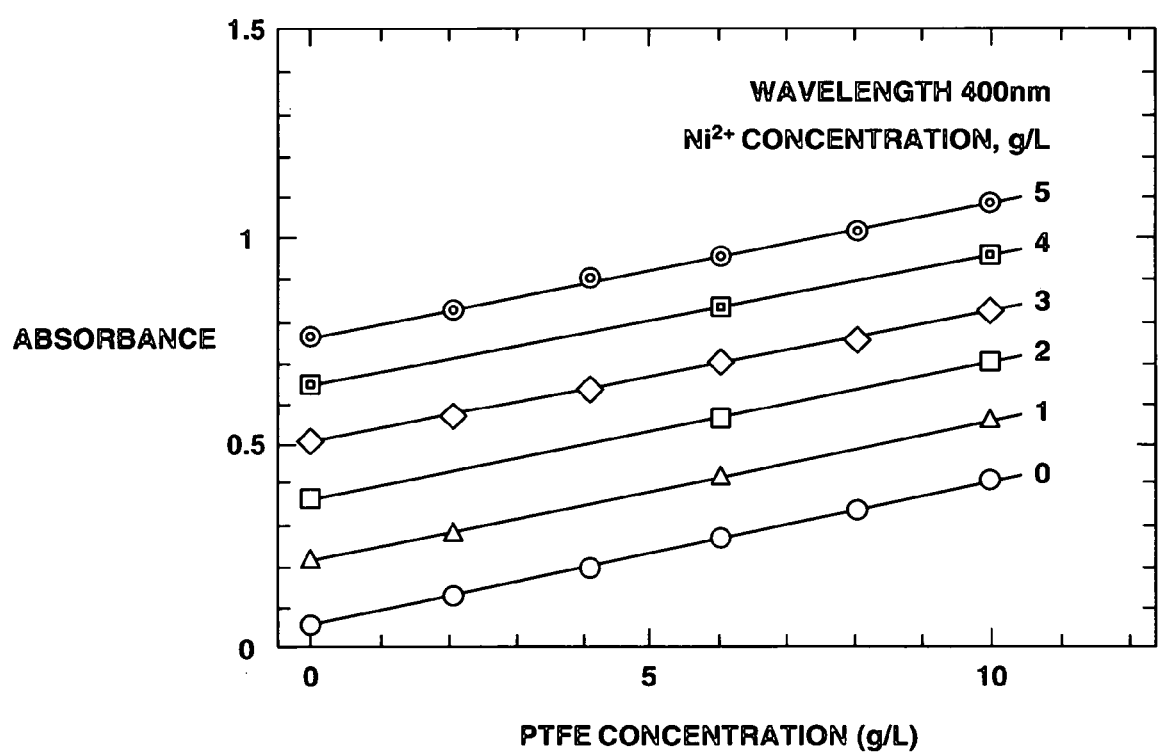
FIG. 5 is a graph showing the relationship between PTFE concentration and absorbance at a wavelength of 400 nm in the case where Ni concentration is varied in the range of 0 to 5 g/L, in an electroless composite nickel plating solution containing PTFE as composite material particles.
Figure 6:
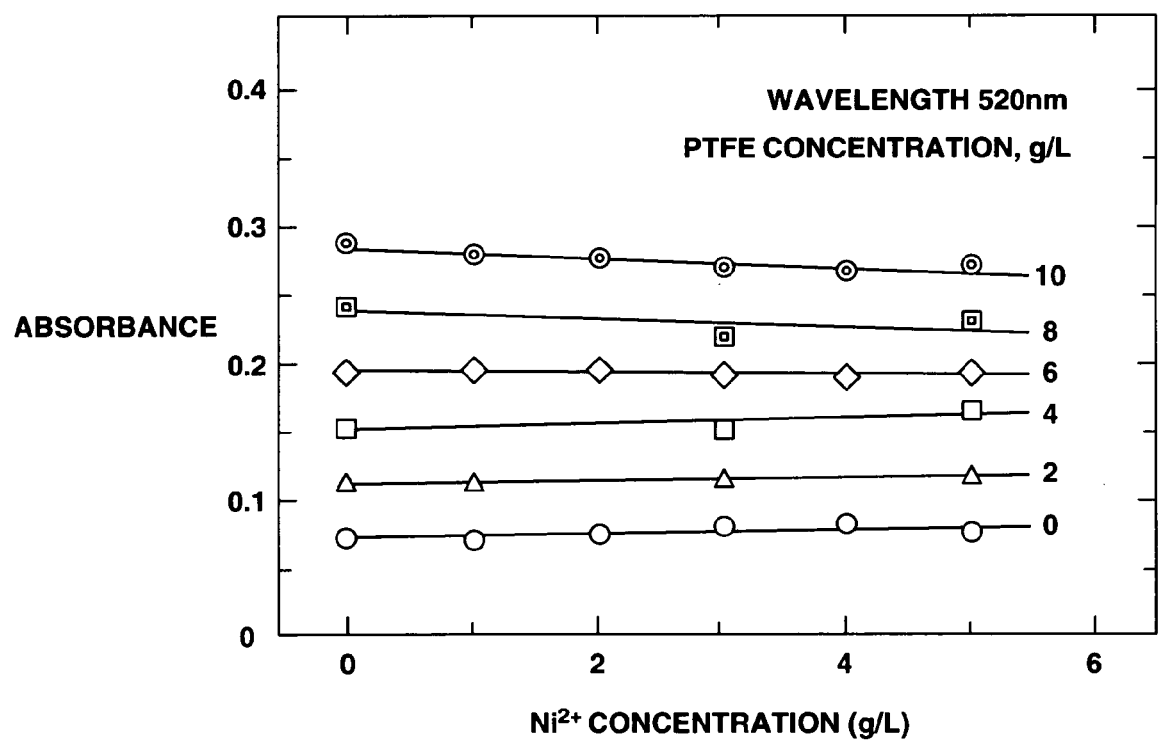
FIG. 6 is a graph showing the relationship between Ni concentration and absorbance at a wavelength of 520 nm in the case where PTFE concentration is varied in the range of 0 to 10 g/L, in an electroless composite nickel plating solution containing PTFE as composite material particles.
Figure 7:
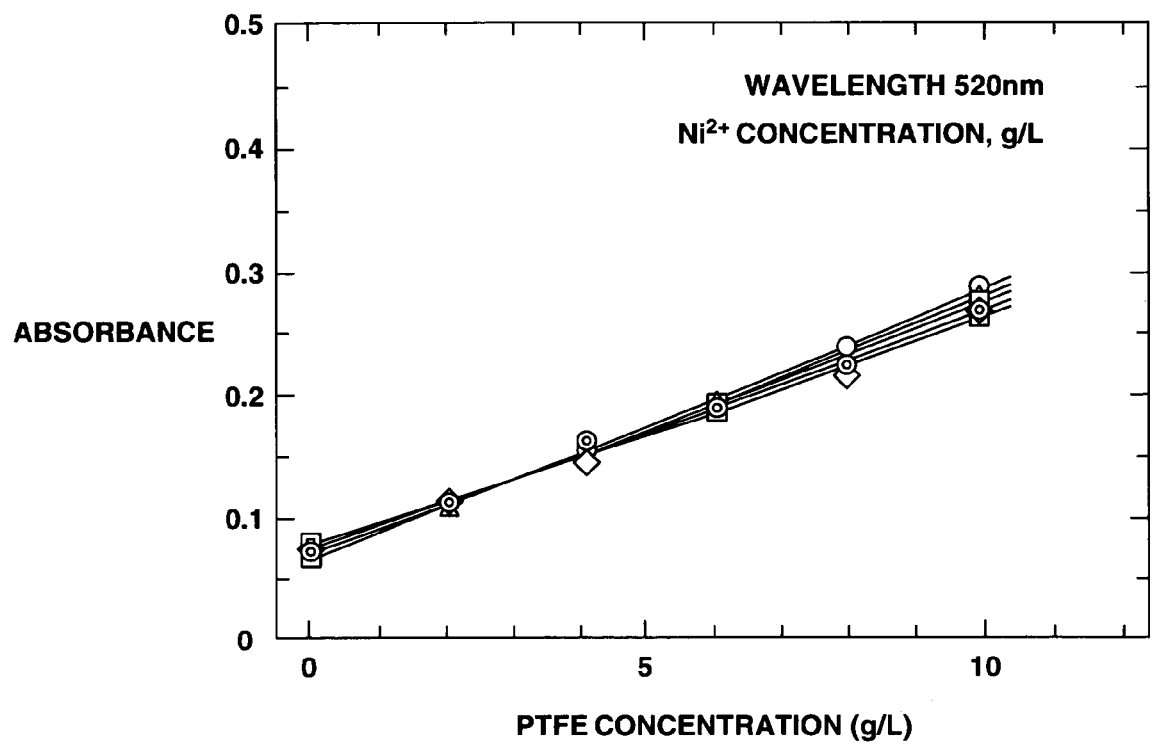
FIG. 7 is a graph showing the relationship between PTFE concentration and absorbance at a wavelength of 520 nm in the case where Ni concentration is varied in the range of 0 to 5 g/L, in an electroless composite nickel plating solution containing PTFE as composite material particles.

FIGS. 1 to 3 are representative examples of absorption patterns obtained when using an electroless Ni—P/PTFE composite plating chemical commercially available from C. Uyemura & Co., Ltd. under the tradename "NIMUFLON", forming sample solutions intentionally changed in Ni concentration and PTFE concentration as electroless Ni—P/PTFE composite plating solutions, and measuring the Ni concentration and PTFE concentration by absorptiometry.

FIG. 1 summarizes absorption patterns obtained for plating solutions gradually changed in Ni concentration, prepared from a plating solution to which a slurry-like PTFE solution (solid content: about 66 wt %) named "NIMUFLON F", a chemical for giving PTFE particles to a plating solution, was not added. Here, the absorbance increases in proportion to the increase in Ni concentration in the wavelength ranges of 350 to 450 nm and 550 to 800 nm.

On the other hand, FIG. 2 summarizes absorption patterns obtained for plating solutions gradually changed in the concentration of NIMUFLON F (slurry-like PTFE solution) with Ni concentration fixed at 0 g/L. The absorbance increases in proportion to the increase in PTFE concentration in all the wavelength range used for measurement, and, particularly characteristic is that the increase tendency of absorbance is acceleratedly increased as the wavelength becomes shorter.

FIG. 3 summarizes absorption patterns obtained for plating solutions gradually changed in the concentration of NIMUFLON F (slurry-like PTFE solution), in the same manner as in FIG. 2, with the Ni concentration fixed at 5 g/L. As seen in FIG. 1, absorption due to Ni is recognized in the wavelength ranges of 350 to 450 nm and 550 to 800 nm; however, the absorbance increases in proportion to the increase in PTFE concentration in all the wavelength range used, and there is also observed the characteristic tendency of accelerated increase in absorbance as the wavelength becomes shorter.

The absorption patterns can be understood as a sum of the absorption pattern of an electroless plating solution with Ni concentration of 5 g/L and the absorption pattern due to the variation in the PTFE concentration as seen in FIG. 2. In order to grasp this more accurately, the absorbance measured at 400 nm and 520 nm in relation to Ni concentration or NIMUFLON F concentration (or PTFE concentration) is summarized in FIGS. 4 to 7. By this, it has been confirmed that the variation in absorbance is in extremely good proportion to both Ni concentration and PTFE concentration, and the absorbance at arbitrary Ni concentration and particle concentration can be understood as a sum of the metallic ion concentration in the plating solution and turbidity due to the dispersed particles. Accordingly, it is suggested that when measurements (formation of analytical curves) for grasping the characteristics of both factors are preliminarily conducted, it is possible to measure the objective Ni concentration while obviating the bad influences of turbidity.

In the electroless composite plating, however, the concentration of dispersed particles and turbidity varies due to various causes other than the preset conditions, for example, such factors as consumption of the plating solution and conditions of sampling, so that large errors are generated unless the factors are grasped at times with a certain degree of accurateness at the time of measurement and reflected on the results of calculation. As a method of coping with this problem, the method constituting the basis of the present invention, namely, the method of obtaining the two unknowns of Ni concentration and turbidity due to the presence of dispersed particles from the results of measurement at least two wavelengths by solving simultaneous equations, is needed.

In view of this, by using the measurement results of FIG. 1 to 7, analytical curves for various combinations of measurement wavelengths were formed, and the extent of generation of errors in the case of assuming an arbitrary plating solution was investigated. As a result of the investigation, it has been found that a combination with which Ni concentration can be calculated with required accuracy under variations of Ni concentration and variations in turbidity, in the method of measuring at two measurement wavelengths, is the combination of measurement at a first wavelength in the wavelength range corresponding to Ni absorption of 350 to 450 nm or 550 to 800 nm, more preferably 370 to 430 nm or 600 to 770 nm, most preferably 390 to 410 nm or 640 to 740 nm, and measurement at a second wavelength not overlapping with the first wavelength in the wavelength range of 250 to 350 nm or 450 to 550 nm, more preferably 275 to 335 nm or 480 to 535 nm, most preferably 300 to 320 nm or 500 to 535 nm, whereby generation of errors can be suppressed.

Here, in the present invention, for a plurality of kinds (preferably, not less than three, more preferably, not less than four) of electroless composite plating solutions in which the concentration of a metallic ion, for example, nickel ion is fixed and the concentration of a composite material, for example, PTFE is varied, absorbance $A_1$ at a first wavelength $WL_1$ and absorbance $A_2$ at a second wavelength $WL_2$ are measured, and from the relationship between the absorbances $A_1$ and $A_2$, the following relational equation is obtained (it is assumed that $A_1 > A_2$).

$$y = \alpha x + \beta$$

Where x: absorbance at second wavelength
y: absorbance at first wavelength
$\alpha$, $\beta$: coefficients On the other hand, for a plurality of kinds (preferably, not less than three, more preferably not less than six) of the electroless composite plating solutions in which the concentration of the metallic ion, for example, nickel ion is varied and the concentration of the composite material, for example, PTFE is also varied, the absorbances $A_1$ and $A_2$ are similarly measured, and from the relationship between K value and the metallic ion concentration, the following relational equation is obtained.

$$M = \gamma K - \delta$$

where M: metallic ion concentration
K: (absorbance at first wavelength)$-\alpha \times$(absorbance at second wavelength)
$\gamma$, $\delta$: coefficients From the relational equation between K value and the metallic ion concentration thus obtained, the metallic ion concentration can be obtained by measuring the absorbances at the first and second wavelengths.

In the case of an alloy-based composite plating solution, a relational equation for a first metallic ion and a second metallic ion alloyable with the first metallic ion is preliminarily obtained, whereby the concentrations of the metallic ions can be obtained. For example, a third wavelength is set, and a relational equation taking into account the influence on the absorbance due to the second metallic ion can be obtained.

Besides, in the case of a copper or cobalt composite plating solution, in the same manner as the case of nickel, a wavelength at which absorption due to copper or cobalt is present and a wavelength at which the absorption due to copper or cobalt is absent are appropriately selected, whereby the concentration of the metallic ion can be analyzed with good accuracy. In the case of copper, transformation to divalent copper ion is preferred.

In putting the system to practical use, spectral separation of light for measurement at a specified wavelength is required. For the spectral separation, use of an interference filter is the most inexpensive and can be the simplest in system structure. However, in the method of spectral separation of light by use of an interference filter, the precision of spectral separation becomes a problem, and the spectrally separated light has a certain width of wavelength. This is expressed as a half-width of wavelength for the interference filter, and is one of qualities. Since a filter with a smaller half-width is a more expensive filter, in order to provide an inexpensive system it is important whether an interference filter with a comparatively large half-width can be selected. In view of this, as the quality of the interference filter required for securing a sufficient analytical accuracy in putting the present invention to practical use, the extent of influence of the half-width was also investigated. As a result of the investigation, it has been found that assuming an interference filter with an arbitrary wavelength in the most preferable wavelength ranges in the above-mentioned two measurement wavelength ranges as a center value, the analytical errors are allowable when the half-width is not more than 100 nm, preferably not more than 50 nm, most preferably not more than 20 nm.

In addition, in the progress of an actual proof test using an absorptiometric unit of a system described later, a sufficient amount of light could not be secured when an interference filter with an extremely small half-width of less than 1 nm was used. To cope with this, more cost is necessarily required for raising the performance of a light-absorbing portion or increasing the light quantity of a light source; thus, it has been found that needless reduction of the half-width of the interference filter not only causes an increase in the cost of the filter itself but also increases the total system cost. Accordingly, it has been judged that the lower limit of the half-width is appropriately not less than 1 nm, more preferably not less than 5 nm, and most preferably not less than 10 nm.

Next, one example of the system according to the present invention will be described referring to FIGS. 8 and 9.

Figure 8:
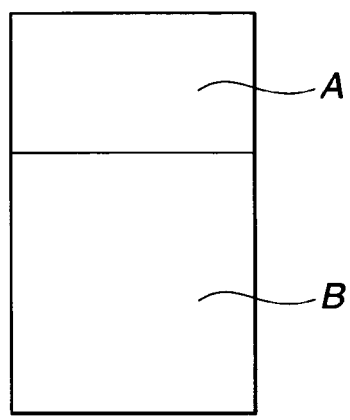
FIG. 8 is a general front view of an automatic analysis and control system according to one embodiment of the present invention.
Figure 9:
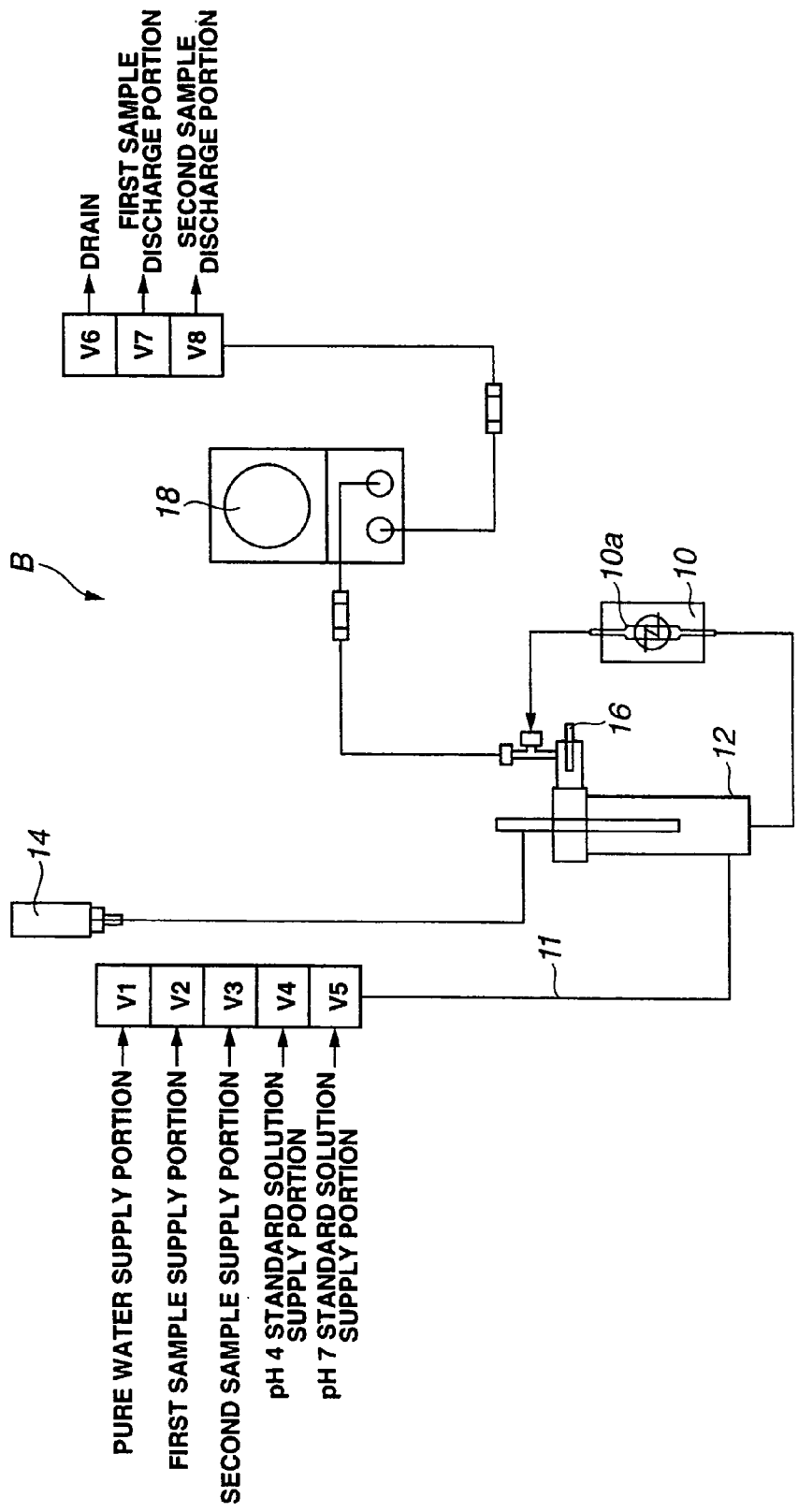
FIG. 9 is an illustration of a measuring portion of the system.

In FIGS. 8 and 9, A is a control portion for controlling arithmetic processing and various operation instructions, and B is a concentration measuring portion; analytical values of an electroless composite plating solution measured by the measuring portion B are transferred to the control portion A, the analytical values are arithmetically processed, and predetermined operation instructions according to the results of arithmetic processing are given to a plating device.

The control portion A incorporates a computer, whereby not only the arithmetic processing, various operation instructions and the like are performed, but also a display mechanism for timedly displaying the analytical results and operation conditions of the system is provided, and setting of control conditions including the setting of the operating conditions of the system and manual operations can be performed. Further, when a personal computer is connected to the control portion through a communication port, main controls such as data processing, operating environments and operation instructions can be performed from the personal computer by use of a software for exclusive use, and a communication line for controlling simultaneously a plurality of communications such as communications with various replenishment units and a temperature controller for controlling the plating temperature can be connected.

As shown in FIG. 9, the measuring portion B comprises an absorbance measuring unit 10 and a pH cell 12. The pH cell 12 is a vertically elongate plating solution dwell portion and a trap portion or a trap mechanism includes the pH cell 12. The piping up to the pH cell 12, i.e., the sampling pipe 11, is 3 mm in inside diameter, and the pH cell 12 is 14 mm in inside diameter. A column 14 for supplying and storing a saturated KCl solution is connected to the pH cell 12, and a temperature sensor 16 is provided. The inside diameter of a tube piped from the place of the temperature sensor 16 and upstream of an absorbance cell 10a is greater than the inside diameter of the absorbance cell 10a, so that the plating solution containing bubbles would not be introduced into the absorbance cell 10a. Though not shown, the absorbance measuring unit 10 comprises a light-receiving portion on one side of the absorbance cell 10a, and a second diaphragm, an interference filter, a primary diaphragm, and a light source lamp in this order from the cell 10a side on the other side. Further, in order that two kinds of interference filters can be automatically changed over with good accuracy, two filters are disposed in a fan form from a shaft of a low-speed motor in the condition of being fixed by axes as short as possible, and a mechanism is provided such that one of the filters is moved to and stopped at a predetermined position in an optical path by rotating the motor forwards or reversely.

In FIG. 9, numeral 18 denotes a sampling pump, and V1 to V8 denote solenoid valves. A pure water supplying portion is connected to the solenoid valve V1, a first sample supplying portion is connected to V2, a second sample supplying portion is connected to V3, a pH 4 standard solution supplying portion is connected to V4, and a pH 7 standard solution supplying portion is connected to V5. The solenoid valve V6 is connected to a drain, V7 is connected to a first sample discharging portion, and V8 is connected to a second sample discharging portion. The solenoid valves V1 to V5 and V6 to V8 are appropriately opened and closed. For example, when the solenoid valves V2 and V7 are opened and other valves are closed and the sampling pump 18 is operated, a first sample from a first plating tank flows through V2 into and through the pH cell 12, where the pH of the first sample is measured, and the sample flows into and through the absorbance measuring unit 10, and flows back into the first plating tank through V7. After the sampling pump 18 is stopped, absorbance is measured at 660 nm, then the interference filter in the absorbance measuring unit 10 is changed over, and absorbance is measured at 520 nm. When V2 is closed and the sampling pump 18 is operated for a predetermined time after the measurement of absorbance is finished, the saturated KCl solution (not shown) flows into and through the pH cell 12 and the absorbance measuring unit 10, and is discharged to the drain by closing V7 and opening V6. These operations are performed at appropriate intervals.

After the analytical operation, calibration and washing are periodically conducted. Calibration of pH electrodes is conducted by introducing the saturated KCl solution, thereafter opening V4, operating the sampling pump 18, causing a pH 4 standard liquid to flow into and through the pH cell 12 and the absorbance measuring unit 10, discharging the pH 4 standard liquid to the drain, then closing V4, opening V5, and causing a pH 7 standard liquid to flow into and through similarly. Thereafter, the above-mentioned analytical operation is conducted. The washing step is conducted by introducing the saturated KCl solution, thereafter closing V5, opening V1, causing pure water to flow into and through the pH cell 12, causing pure water to flow into and through the absorbance measuring unit 10, discharging pure water to the drain, and measuring absorbance for pure water at two wavelengths in the same manner as above.

Next, the results of various actual-proof tests conducted using the system will be described.

First, as for the measurement wavelength, a conventional automatic analysis and control system for electroless nickel plating solution in many cases uses an arbitrary wavelength in the range of 600 to 800 nm as a measurement wavelength. The reason for this is that in the performance of a light source and a light-receiving portion, there is the tendency that a sufficient light quantity is easily secured at a comparatively longer wavelength in the visible region. Accordingly, the present inventor selected a wavelength of 660 nm as one measurement wavelength. Further, as the second measurement wavelength, a wavelength of 520 nm at which absorption due to Ni concentration is substantially absent was selected in the same manner as in the above-mentioned basic investigation, and an investigation was carried out at the two measurement wavelengths.

First, formation of analytical curves for this system was carried out for several kinds of electroless Ni—P/PTFE composite plating solutions, in the same manner as shown in FIGS. 1 to 7 above. As one example of this, the results with the NIMUFLON plating solution in the same manner as above are shown in Table 1 and FIGS. 10 and 11, whereas the results with NIMUFLON FUL plating solution (a product by C. Uyemura & Co., Ltd.) having a different base liquid composition are shown in Table 2 and FIGS. 12 and 13.

TABLE 1

| Sample No. | Measurement of 100% transmissivity (pure water) | | Measurement of plating solution | | Measurement of % transmissivity after calibration | | Absorbance ABS | | Manually analyzed value | | | K value ABS (660) −0.7116 × ABS (520) | Calculated value 27.652 × K − 1.4267 | Error |
|---|---|---|---|---|---|---|---|---|---|---|---|---|---|---|
| | | | | | | | | | Ni Concentration (g/L) | pH value | PTFE Concentration (g/L) | | | |
| | 660 nm | 520 nm | 660 nm | 520 nm | 660 nm | 520 nm | 660 nm | 520 nm | | | | | | |
| 1 | 106.9 | 100.6 | 57.2 | 78.9 | 53.5 | 78.4 | 0.27158 | 0.10552 | 4.00 | 5.12 | 3.5 | 0.1964929 | 4.01 | 0.01 |
| 2 | 106.8 | 100.5 | 54.7 | 78.8 | 51.2 | 78.4 | 0.29059 | 0.10564 | 4.53 | 5.10 | 3.5 | 0.2154106 | 4.53 | 0.00 |
| 3 | 106.8 | 100.5 | 49.8 | 77.5 | 46.6 | 77.1 | 0.33134 | 0.11286 | 5.52 | 5.08 | 3.5 | 0.2510276 | 5.51 | −0.01 |
| 4 | 106.8 | 100.5 | 46.6 | 76.0 | 43.6 | 75.8 | 0.36019 | 0.12135 | 6.14 | 5.08 | 3.5 | 0.2738309 | 6.15 | 0.01 |
| 5 | 106.8 | 100.5 | 51.8 | 77.7 | 48.5 | 77.3 | 0.31424 | 0.11175 | 5.03 | 5.09 | 3.5 | 0.2347237 | 6.08 | 0.00 |
| 6 | 106.8 | 100.5 | 58.3 | 86.9 | 52.7 | 86.5 | 0.27806 | 0.06315 | 5.03 | 5.09 | 0.0 | 0.233128 | 5.02 | −0.01 |
| 7 | 106.7 | 100.5 | 52.9 | 79.8 | 49.6 | 79.4 | 0.30471 | 0.10016 | 5.04 | 5.09 | 2.5 | 0.2334326 | 5.03 | −0.01 |
| 8 | 106.8 | 100.5 | 50.8 | 75.8 | 47.6 | 75.4 | 0.32271 | 0.12250 | 5.07 | 5.09 | 4.5 | 0.2355388 | 5.09 | 0.02 |
| 9 | 106.9 | 100.5 | 49.2 | 71.6 | 46.0 | 71.2 | 0.33704 | 0.14725 | 5.03 | 5.09 | 6.0 | 0.2322273 | 4.99 | −0.04 |

TABLE 2

| Sample No. | Measurement of 100% transmissivity (pure water) | | Measurement of plating solution | | Measurement of % transmissivity after calibration | | Absorbance ABS | | Manually analyzed value | | | K value ABS (660) −0.6765 × ABS (520) | Calculated value 27.857 × K − 1.4267 | Error |
|---|---|---|---|---|---|---|---|---|---|---|---|---|---|---|
| | | | | | | | | | Ni Concentration (g/L) | pH value | PTFE Concentration (g/L) | | | |
| | 660 nm | 520 nm | 660 nm | 520 nm | 660 nm | 520 nm | 660 nm | 520 nm | | | | | | |
| 1 | 106.7 | 100.2 | 60.9 | 83.2 | 57.1 | 83.0 | 0.24355 | 0.08074 | 3.55 | 4.91 | 3.0 | 0.18892354 | 3.54 | −0.01 |
| 2 | 106.7 | 100.0 | 57.0 | 81.9 | 53.4 | 81.9 | 0.27229 | 0.08672 | 4.05 | 4.90 | 3.0 | 0.21362612 | 4.07 | 0.02 |
| 3 | 106.5 | 99.9 | 50.2 | 79.8 | 47.1 | 79.9 | 0.32665 | 0.09756 | 5.15 | 4.86 | 3.0 | 0.26064479 | 5.15 | 0.00 |
| 4 | 106.5 | 100.0 | 47.8 | 79.2 | 44.9 | 79.2 | 0.34792 | 0.10127 | 5.61 | 4.89 | 3.0 | 0.2794093 | 5.58 | −0.03 |

TABLE 2-continued

| Sample No. | Measurement of 100% transmissivity (pure water) | | Measurement of plating solution | | Measurement of % transmissivity after calibration | | Absorbance ABS | | Manually analyzed value | | | K value ABS (660) −0.6765 × ABS (520) | Calculated value 27.857 × K − 1.4267 | Error |
|---|---|---|---|---|---|---|---|---|---|---|---|---|---|---|
| | 660 nm | 520 nm | 660 nm | 520 nm | 660 nm | 520 nm | 660 nm | 520 nm | Ni Concentration (g/L) | pH value | PTFE Concentration (g/L) | | | |
| 5 | 106.5 | 100.0 | 53.4 | 80.9 | 50.1 | 80.9 | 0.29981 | 0.09205 | 4.61 | 4.88 | 3.0 | 0.23753553 | 4.82 | 0.01 |
| 6 | 106.5 | 99.9 | 56.2 | 86.8 | 52.8 | 86.9 | 0.27761 | 0.06105 | 4.58 | 4.88 | 0.0 | 0.23631583 | 4.59 | 0.01 |
| 7 | 106.6 | 100.0 | 55.1 | 84.0 | 51.7 | 84.0 | 0.28661 | 0.07572 | 4.56 | 4.88 | 1.5 | 0.23538054 | 4.57 | 0.01 |
| 8 | 106.0 | 99.4 | 52.2 | 78.4 | 49.2 | 78.9 | 0.30764 | 0.10307 | 4.60 | 4.88 | 4.0 | 0.23790829 | 4.63 | 0.03 |
| 9 | 106.6 | 100.2 | 52.1 | 77.3 | 48.9 | 77.1 | 0.31092 | 0.11269 | 4.55 | 4.88 | 5.0 | 0.2346859 | 4.55 | 0.00 |

Figure 10:
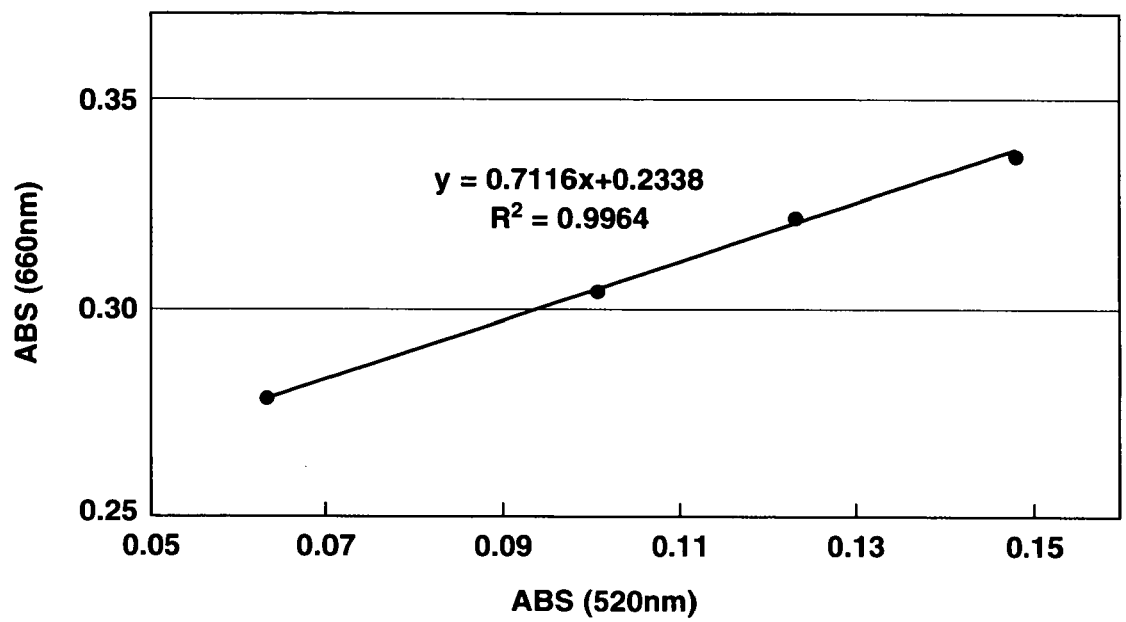
FIG. 10 is a graph showing the relationship between absorbance at a wavelength of 660 nm and absorbance at a wavelength of 520 nm measured by the system for an electroless composite nickel plating solution in which Ni concentration is fixed and PTFE concentration is varied.
Figure 12:
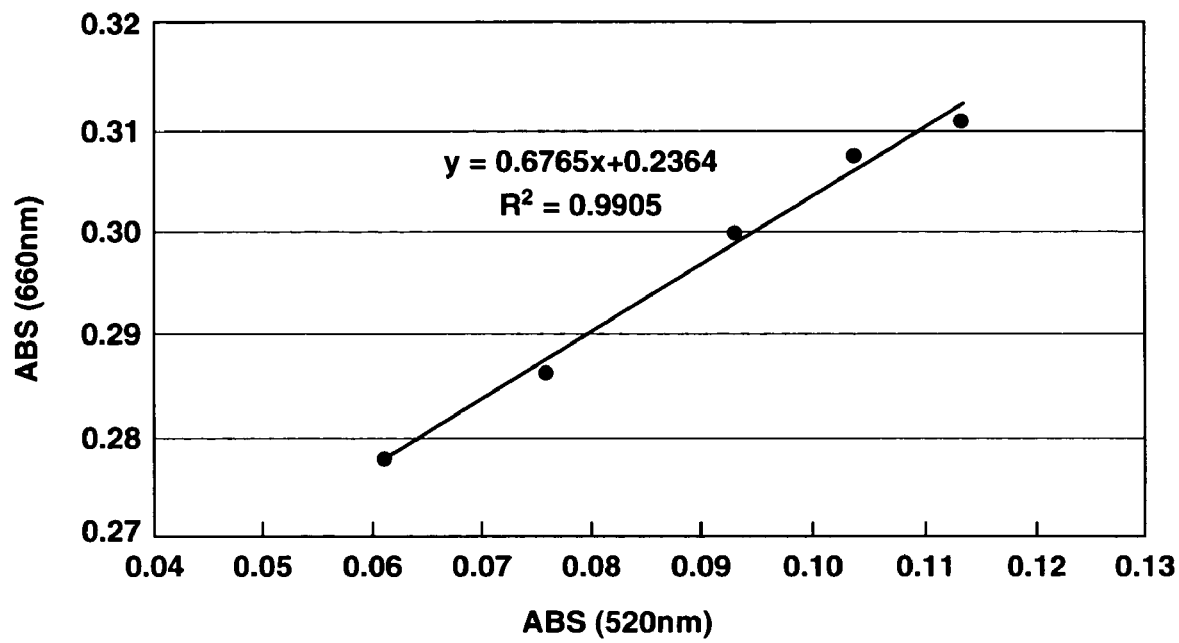
FIG. 12 is a graph showing the relationship between absorbance at a wavelength of 660 nm and absorbance at a wavelength of 520 nm measured by the system for another electroless composite plating solution in which Ni concentration is fixed and PTFE concentration is varied.

Here, FIGS. 10 and 12 show the relationship between the absorbance (ABS) at a wavelength of 660 nm and the absorbance (ABS) at a wavelength of 520 nm for samples (sample No. 5 to 9) changed in PTFE concentration with Ni conncentration fixed, in NIMUFLON and NIMUFLON FUL plating solutions, respectively, and there are given the following relationships:

FIG. 10: $y=0.7116x+0.2338, R^2=0.9964$

FIG. 12: $y=0.6765x+0.2364, R=0.9905$

Figure 11:
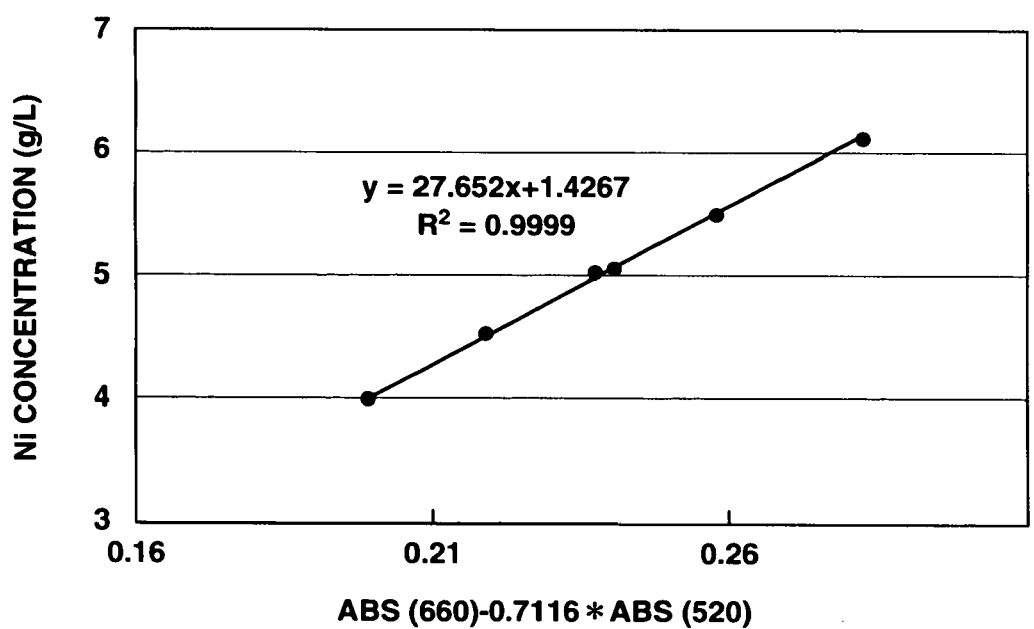
FIG. 11 is a graph showing the relationship between K value and Ni concentration for the electroless composite nickel plating solution.
Figure 13:
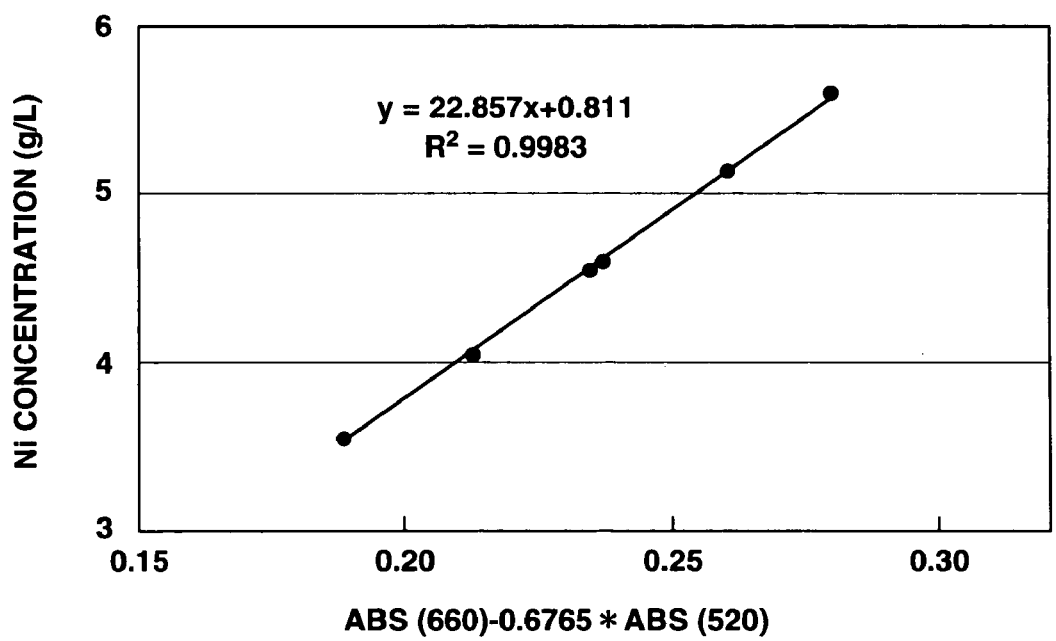
FIG. 13 is a graph showing the relationship between K value and Ni concentration for the electroless composite nickel plating solution.

On the other hand, FIGS. 11 and 13 show the relationship between K value and Ni concentration for sample No. 1 to 9. In this case, the K value is represented by $$K\ value = ABS(660) - \alpha \times ABS(520)$$

where ABS(660): absorbance at wavelength of 660 nm
ABS(520): absorbance at wavelentth of 520 nm
α: coefficient of relational equation X obtained from FIGS. 10 and 12, namely, 0.7116 in the case of NIMUFLON of FIG. 10 and 0.6765 in the case of NIMUFLON FUL FIG. 12.

Therefore, from FIGS. 11 and 13, there are respectively given the following relational equations:

FIG. 11: $Ni=27.652 \times [ABS(660)-0.7116 \times ABS(520)]-1.4267, R^2=0.9989$ FIG. 13: $Ni=22.857 \times [ABS(660)-0.6765 \times ABS(520)]-0.811, R^2=0.9983$ The relational equations obtained from FIGS. 11 and 13 are equations constituting analytical curves for obtaining the Ni concentration by use of two absorbances, namely, the absorbance at 660 nm (ABS 660) and the absorbance at 520 nm (ABS 520), obtained upon measurement of absorbance at two measurement wavelengths for actual samples having unknown Ni concentration and PTFE concentration, in NIMUFLON and NIMUFLON FUL, and is a calculational equation used at the time of arithmetic treatment by the system. In the two kinds of electroless Ni—P/PTFE composite plating solutions shown as examples, good proportionality relationship exists for the Ni concentration and PTFE concentration, in the same manner as in the results of the basic investigation above, and the difference between the Ni concentration deduced from the final calculational equation and the value obtained by separate titration analysis is at most 0.04 g/L, which shows an extremely high accuracy.

As a reference, a simulation was conducted to know what degree of errors would be generated due to influence of turbidity in the case of calculating the Ni concentration from the measurement of absorbance at one wavelength, here at 660 nm, in the same manner as in the conventional general system for electroless plating. The results of the simulation suggested that an error on the order of 0.8 g/L would be generated at maximum. This shows that the use of two measurement wavelengths enhances the analytical accuracy by about 20 fold, based on simple calculation, and, thus, a very high effect has been verified.

Next, the results of a test of actually conducting automatic analysis and control on an electroless composite plating solution by use of the above-mentioned system and the above-mentioned relational equations will be described. As a representative example, a NIMUFLON FUL plating solution (PTFE concentration: 4.0 g/L; the PTFE content of the electroless plating film obtained was 25 vol %) as electroless Ni—P/PTFE composite plating was used, and, while continuously replenishing Ni ion (nickel sulfate), sodium hypophosphite and PTFE to maintain the concentrations of these components at substantially fixed values from the time of forming the plating bath and while replenishing sodium hydroxide to maintain a substantially fixed pH, running was conducted up to MTO (the number of turns; one turn corresponds to the time when 4.46 g of $Ni^{2+}$ per 1 L of plating bath has been consumed or deposited, and this is an index indicating the degree of aging of the electroless nickel plating solution), and Ni concentration analysis was carried out at appropriate intervals. The amount of the plating solution was 50 L. The results are shown in Table 3 and FIGS. 14 to 17. For example, in the case of FIG. 16, the value obtained by dividing the coefficient of x in the linear equation, namely, 0.1165 by the Ni concentration standard value of 4.5 (g/L) can be made to be a correction coefficient for one turn, and the value obtained by multiplying the Ni concentration in the system in one turn by $$1+(0.1165 \div 4.5)=1.026$$

can be made to be the Ni concentration after correction.

TABLE 3

| | Ni concentration | | | pH | | | Turbidity | Ni concentration after turn correction | |
|---|---|---|---|---|---|---|---|---|---|
| MTO | System (uncorrected) | Manual analysis | Error | System | Manual analysis | Error | (%) 550 nm | After correction | Error |
| 0.00 | 4.46 | 4.49 | −0.03 | 4.84 | 4.88 | −0.04 | 79.7 | 4.49 | 0.00 |
| 0.43 | 4.48 | 4.55 | −0.07 | 4.87 | 4.91 | −0.04 | 80.2 | 4.55 | 0.00 |
| 0.72 | 4.47 | 4.58 | −0.11 | 4.85 | 4.91 | −0.06 | 80.8 | 4.57 | −0.01 |
| 1.08 | 4.51 | 4.63 | −0.12 | 4.84 | 4.90 | −0.06 | 80.7 | 4.64 | 0.01 |
| 1.24 | 4.41 | 4.58 | −0.17 | 4.82 | 4.88 | −0.06 | 81.3 | 4.58 | 0.00 |
| 1.58 | 4.31 | 4.52 | −0.21 | 4.88 | 4.86 | 0.02 | 81.9 | 4.51 | −0.01 |
| 1.89 | 4.29 | 4.54 | −0.25 | 4.85 | 4.85 | 0.00 | 82.1 | 4.52 | −0.02 |
| 2.25 | 4.30 | 4.57 | −0.27 | 4.87 | 4.86 | 0.01 | 82.6 | 4.57 | 0.00 |
| 2.56 | 4.24 | 4.54 | −0.30 | 4.87 | 4.85 | 0.02 | 83.3 | 4.53 | −0.01 |
| 2.76 | 4.16 | 4.47 | −0.31 | 4.87 | 4.86 | 0.01 | 83.7 | 4.48 | 0.01 |

Figure 14:
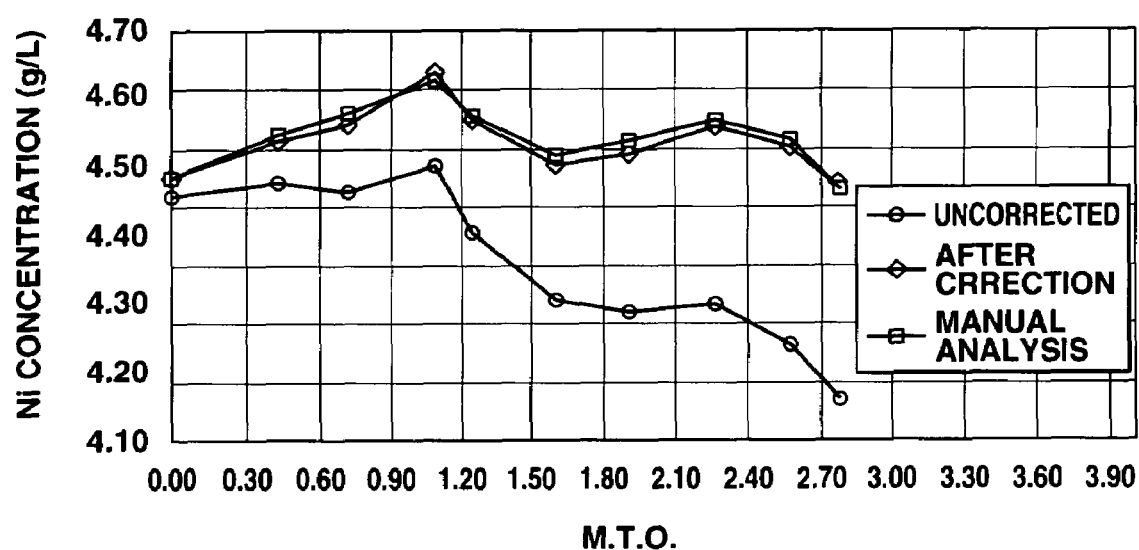
FIG. 14 is a graph showing the relationship between the number of turns (MTO) and measured value of Ni concentration in the case where electroless composite nickel plating is conducted continuously.
Figure 15:
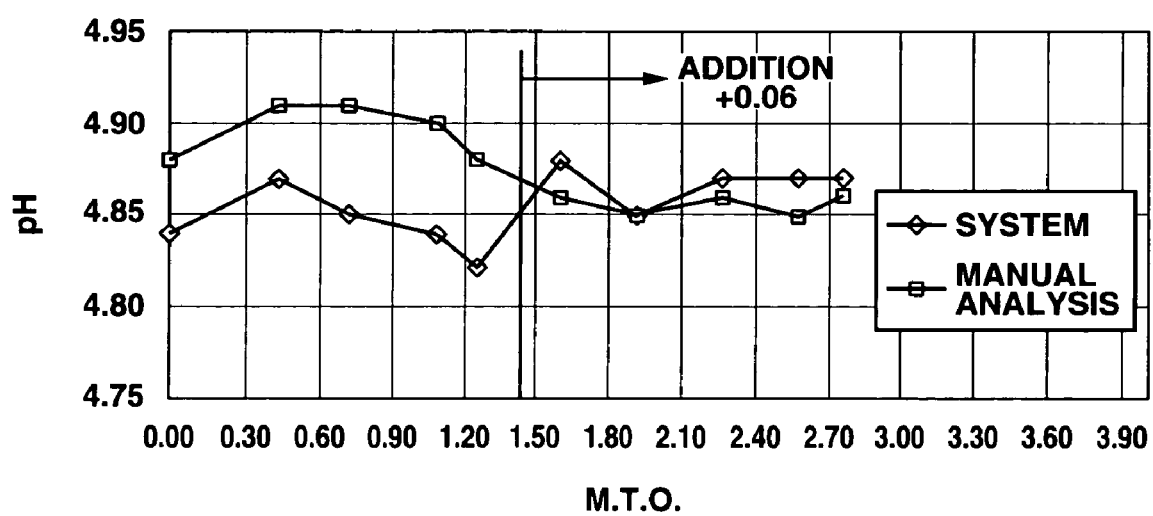
FIG. 15 is a graph showing the relationship between the number of turns and measured value of pH in the case where electroless composite nickel plating is conducted continuously.

Table 3 summarizes representative values of the analytical results, the results concerning Ni concentration are summarized in FIG. 14, and the results concerning pH are summarized in FIG. 15. There were no large errors between the value obtained by manual analysis of the Ni concentration in the plating solution during running and the uncorrected value obtained by the analysis by the above-mentioned system. As the running proceeded, however, there was a tendency that the errors are enlarged to an innegligible level. The cause of this is that as the electroless composite nickel plating solution is used, phosphite and sulfate are accumulated as aged accumulated components in the plating solution, and the degree of absorption by Ni complex ion is gradually reduced. There are some electroless composite plating solutions of such a type that the degree of absorption is gradually increased, reversely to the pattern shown here. In that case, the electroless plating solution is of such a type that the complexing agent is increased by replenishment in a degree of overcoming the lowering in the degree of absorption due to the aged accumulated matter. In the case of a commercially available electroless plating solution, this problem can be solved by preliminarily grasping the inclination of the plating solution and conducting an appropriate correction on the analyzed values. In fact, in the case of the NIMUFLON FUL plating solution shown here as an example, a predetermined correction comprising some addition as well as the proportional correction coefficient results in that the value after correction in FIG. 14 roughly overlap with the manually analyzed value, thereby showing good accuracy.

Figure 16:
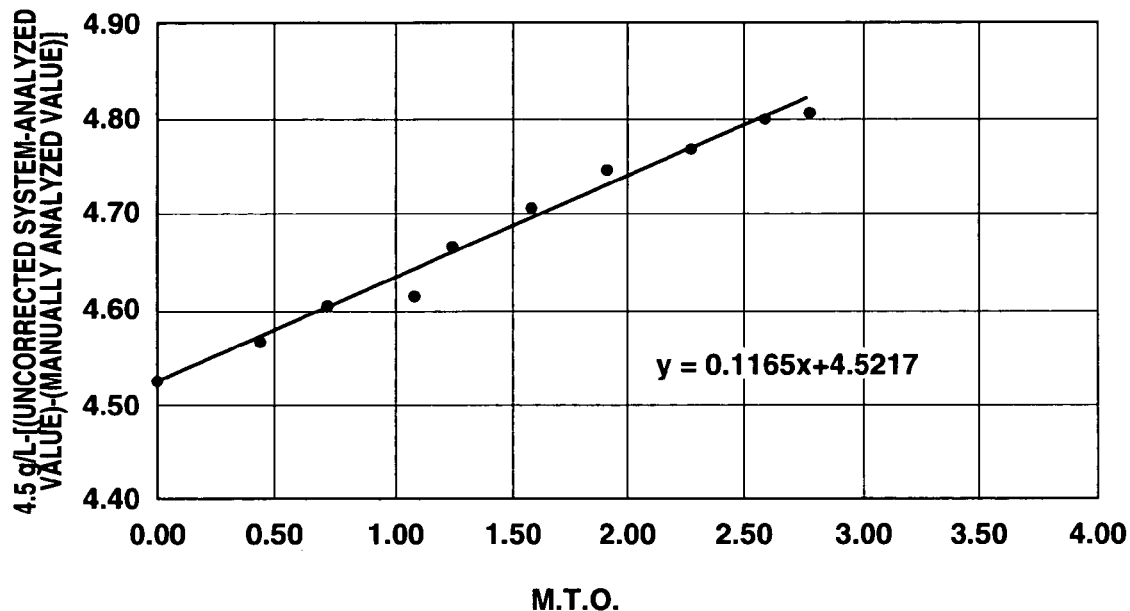
FIG. 16 is a graph for calculating a turn correction coefficient and shows the relationship between the number of turns and Ni concentration standard value minus error value.

As for the calculation of the correction coefficient, as shown in FIG. 16, a graph obtained by plotting the value obtained by subtracting the error (namely, uncorrected system-analyzed value minus manually analyzed value) from the Ni concentration standard value (for example, 4.5 g/L) against the number of turns shows a proportionality relationship, and the correction coefficient can be deduced from the linear equation.

On the other hand, as to the value of pH which is important control item of the plating solution, there arises a certain error due to the system. As shown in FIG. 15, correction was not conducted up to about 1.4 turns, so that there was an error of about 0.06 between the manually analyzed value and the system-analyzed value, but, after the correction, the error was reduced to an allowable level.

Figure 17:
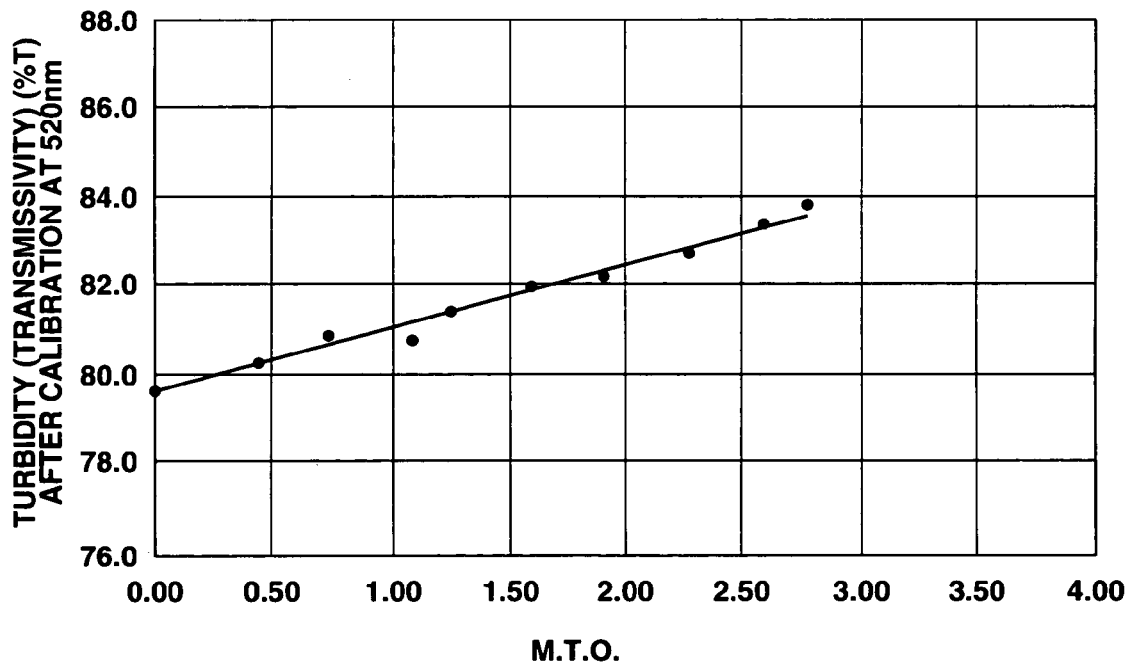
FIG. 17 is a graph showing the relationship between the number of turns and turbidity measured at 520 nm in the case where electroless composite nickel plating is conducted continuously.

The results shown in FIG. 17 are a summary of transmissivity measured at a measurement wavelength of 520 nm varied due mainly to turbidity measured on the system, in relation to turn. Actually, the amount of PTFE particles in the plating solution gradually increases due to replenishment as the turn proceeds. This leads to an expectation that the transmissivity is gradually lowered, but, actually, there is a tendency that the transmissivity gradually increases and turbidness decreases. Again, this change arises from accumulation of the aged matter mentioned above. This change is present as a large variation in transmissivity of about 4%, up to about 2.6 turns. If measurement at one wavelength were conducted by neglecting this variation, the error due to the variation might reach to an error of about 1.0 g/L. It can be understood from the results that, not only the measurement at two wavelengths, the existing various turn correction functions of a general electroless plating system conventionally commercialized are necessarily required, as far as the electroless plating solution as a base liquid is commonly used.

On the other hand, there are cases where a specific trouble is generated during running with various plating solutions. The trouble is that the analytical value of Ni concentration abruptly shows an abnormally high value. Though the cause of this trouble was not specified in the beginning, investigations and studies of the cause have revealed that this trouble comes from the following causes.

(1) The bubbles contained in the plating solution sampled and transported into the absorption cell were not sufficiently separated in the short time from the stop of the sampling to the measurement of absorbance, so that the value in the measurement of absorbance would easily vary, resulting in lowering of analytical accuracy. The causes of such troubles include the kind of composite plating solution and aging of the plating solution.

(2) The chemical replenishing position and the plating solution sampling position were close to each other, so that sampling was conducted in the condition where the chemical was not sufficiently diffused uniformly, resulting in that the analytical value was abnormally high.

(3) The stability of an interference filter change-over mechanism was insufficient, so that an error was generated by a bit of vibration or shock on the system.

Against these causes of troubles, the following countermeasures are effective.

(1) In order to suppress as possible the pick-up of bubbles into the absorption cell, a trap portion for easier separation of the bubbles consisting of a vertically elongate plating solution dwell portion having a cross-sectional area of not less than two times that of a sampling piping is provided at an appropriate place in the system piping extending to the absorption cell. In concrete, an inlet for feeding the plating solution into the pH cell is provided at an upper portion of the pH cell, and an outlet is provided at a lower portion. The pH cell has a cross-sectional area much larger than that of the sampling tube, and flow velocity is extremely lowered in this portion, so that larger bubbles can escape to the upper portion of the pH cell. On the other hand, the bubbles are comparatively fewer at the lower portion of the pH cell, so that the plating solution with less bubbles is easily supplied to the absorption cell located on the downstream side of the lower portion of the pH cell.

(2) In order to perform measurement of absorbance by eliminating as possible the influence of the bubbles fed into the absorption cell, the time from the stop of sampling of the plating solution to the start of absorbance measurement is set to be not less than 15 sec.

The expression "from the stop of sampling" means, for example, after the sampling pump 18 is stopped after the first or second sample is caused to flow into the absorbance measuring unit 10 by the sampling pump 18 in the system shown in FIG. 9.

(3) The sampling position is set as far as possible from the position where chemicals are replenished automatically.

(4) An improvement in the interference filter change-over mechanism for increasing the operation control and mechanical strength is conducted, thereby suppressing the variation of the stop position and influences of vibration and shock.

By these improvements, generation of an abnormal analytical value is substantially prevented. Particularly, the elongation of the standing time from the stop of sampling to the start of absorbance measurement according to the countermeasure (2) is effective. When a standing time of not less than 15 sec is secured, variation was suppressed to a substantially allowable level. The standing time is more preferably not less than 30 sec, and most preferably not less than 60 sec. It is ideal that the standing time is as long as possible, but there is need for analysis frequency for the plating solution and the analysis interval is about 120 sec on the minimum side; therefore, the standing time cannot be elongated needlessly.

Another intrinsic problem in building up an automatic analysis and control system for a composite plating solution is the contamination of the absorption cell by adhesion of dispersed particles. The contamination of the absorption cell is a cause of variation of transmissivity or absorbance, in the same manner as the dispersed particles in the plating solution. Analysis at a plurality of measurement wavelengths according to the present invention gives an improving effect on this problem, but the contamination by adhesion of dispersed particles to the absorption cell occurs on a level incomparable to the case of a general electroless plating solution. In order to solve this problem, it is desirable to carry out washing at a comparatively high frequency. However, in order to wash the absorption cell incorporated in the system, much labor for detaching the cell from the system and the like is taken. Further, the contaminants adhered tend to be considerably difficult to remove, so that ultrasonic washing, use of an acidic (hydrochloric acid, nitric acid or the like) or basic (caustic soda, ammonia or the like) solution, together with a detergent, washing with an organic solvent such as ethanol, or the like is required. Although the system is provided with contrivances on design basis such as one for easy detachment of the cell, incorporation of an ultrasonic device or a mechanism for feeding the above-mentioned cleaning liquid into the automatic analysis and control system for the purpose of automatic washing of the inside surface of the absorption cell has a large demerit on a cost basis, and complicates the structure of the system. Further, generation of a waste liquid such as acid, alkali, organic solvent or the like is a high burden on the user. Thus, this approach is substantially impossible.

As described above, the analysis at a plurality of measurement wavelengths is indispensable because the turbidity of the plating solution as the object of analysis may possibly vary on each analysis. However, the contamination of the absorption cell in many cases leads to comparatively mild variation, and the major problem in this case is only the error due to variation of the standard of 100% transmissivity or zero absorbance for pure water, which is corrected to a certain degree by the measurement at least two or more measurement wavelengths. For this purpose, it is necessary to measure using one absorption cell. When, for example, an absorbance measuring unit is so designed as to provide absorption cells for each measurement wavelength, if a difference in the degree of contamination is generated after measurement of the standard value with pure water, large errors are generated in the analytical values thereafter. Accordingly, it is important to periodically measure the standard value of 100% transmissivity or zero absorbance by using pure water, and this problem is sufficiently alleviated in the case of the system in the above-mentioned example.

For example, by calculating the analytical results of the plating solution carried out next according to "(transmissivity with pure water)/100×(transmissivity of analytical sample)", the error due to contamination of the absorption cell can be alleviated. In order to prevent the contamination of the absorption cell from becoming so heavy as to have influence on the analytical results, it is possible to issue an alarm to prompt washing or replacement of the absorption cell when the transmissivity with pure water varies from the precedent measured value of transmissivity with pure water by not less than a predetermined extent (for example, not less than 1%).

Figure 18:
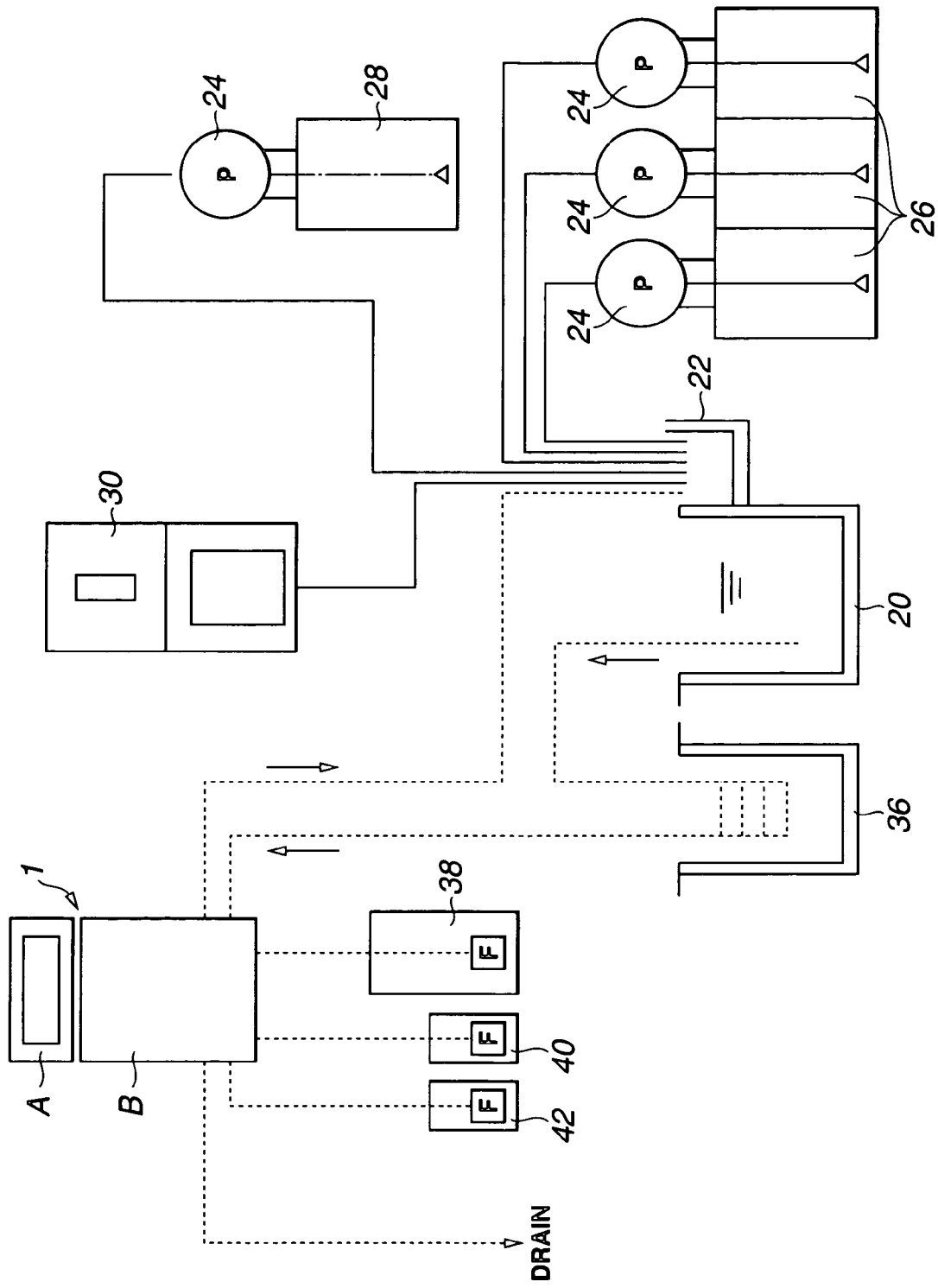
FIG. 18 is a general view showing one example of an electroless composite plating system in which the system of the present invention is incorporated.
Figure 19:
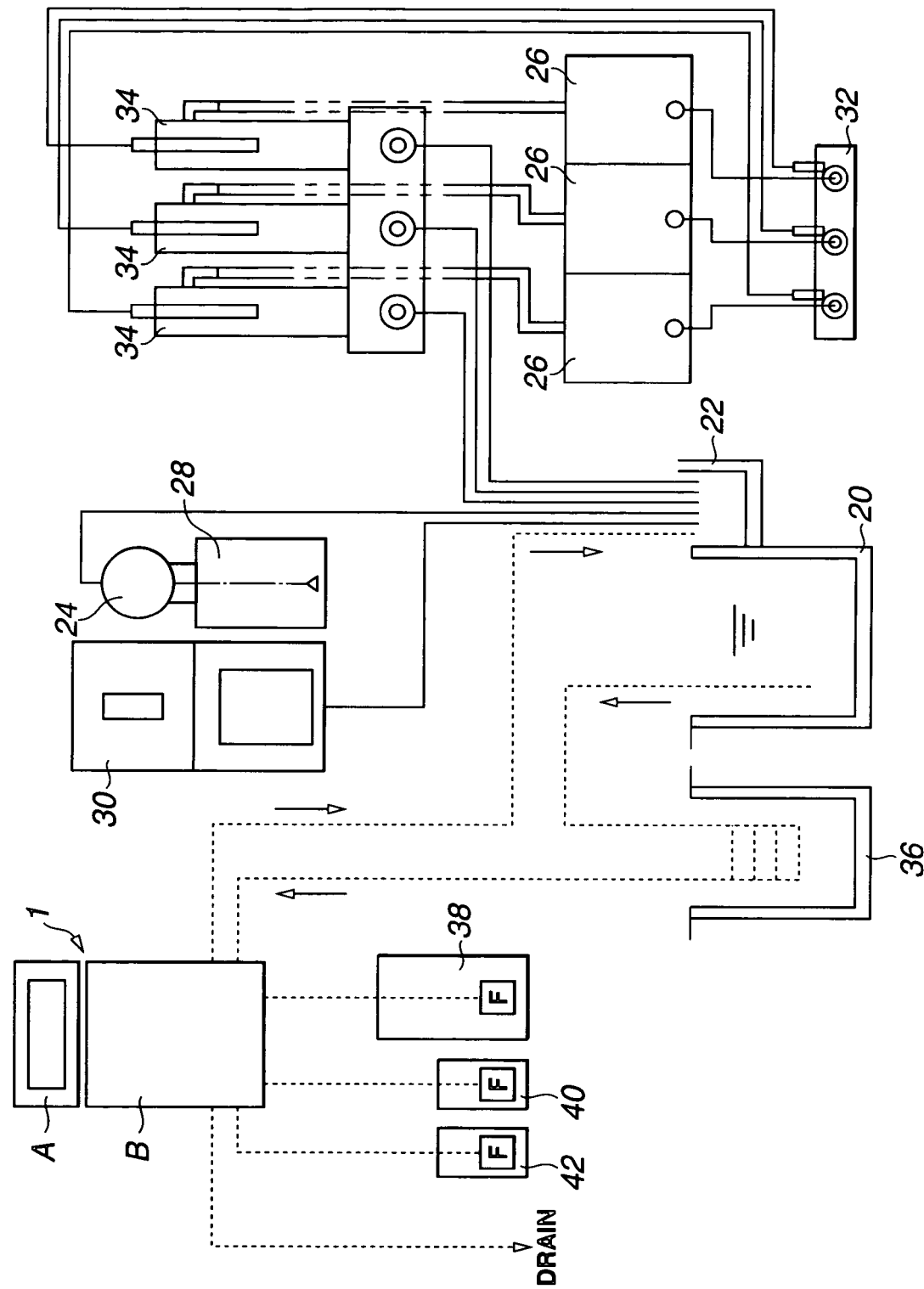
FIG. 19 is a general view showing another example of an electroless composite plating system in which the system of the present invention is incorporated.

FIGS. 18 and 19 show an example of the plating device in which the present system is incorporated. Namely, FIG. 18 shows an example in which chemical liquids as main components are replenished mainly by using fixed-quantity pumps. Merits of the fixed-quantity pump type are that equipment cost is comparatively low, the replenishing amount can be controlled through operating time, and the replenishing amount can be controlled arbitrarily and automatically for each set of analytical results. On the other hand, FIG. 19 shows an example in which the chemical liquids as main components are fed by columns, the merit of which is higher stability of metering of the replenishing amount than the fixed-quantity pump.

Here, in FIG. 18, numeral 20 denotes a plating tank, to which an overflow tank 22 is annexed. Numeral 24 denotes a fixed-quantity pump, 26 denotes a replenishing agent (nickel salt, reducing agent, complexing agent or the like) tank, 28 denotes an alkali supply tank, and 30 denotes a composite material supply column. The replenishing agents, the alkali and the composite material are supplied into the overflow tank, and are caused to flow into the plating solution in the plating tank. In FIG. 19, numeral 32 denotes a fixed-quantity pump, 34 denotes a replenishing column, and other features than the replenishment of main replenishing agents by use of columns are the same as in FIG. 18.

On the other hand, in FIGS. 18 and 19, numeral 36 denotes a cooling mechanism, where the plating solution is cooled to room temperature, before being supplied to the automatic analysis and control system 1, where analysis is conducted as described above. In the figure, 38 denotes a pure water tank, 40 denotes a pH 4 standard liquid tank, and 42 denotes a pH 7 standard liquid tank.

As has been described above, supplied with analytical values from a concentration measuring portion B, a control portion A calculates analytical results. According to the analytical results, the control portion A controls operations of the fixed-quantity pumps 24 and the composite material supply column 30. For example, when it is seen from the analytical results that the metal concentration is insufficient, the fixed-quantity pump 24 at the replenishing agent tank is operated for a preset time, and is stopped. Alternatively, the fixed-quantity pump 24 at the replenishing agent tank is operated, and is stopped when it is seen from the analytical results thereafter that the insufficiency of the metal concentration has been cleared. The operation of the fixed-quantity pump 24 at the alkali supply tank for pH control is also controlled in the same manner. As for the control of the composite material supply column, for example, the column is operated once when the number of times of the operation of the fixed-quantity pump for the replenishing agent has reached a predetermined number of times; alternatively, the amount of metal replenished into the plating solution is calculated from the operating time of the fixed-quantity pump 24 for the replenishing agent, and the composite material supply column is operated once when the amount of metal replenished has reached a predetermined amount. By this, a predetermined amount of metal is replenished into the plating solution.

According to the present invention, the concentration of a metallic ion in an electroless composite plating solution can be automatically analyzed easily and securely.

The invention claimed is:

1. An automatic analysis and control method for measuring the concentration of a metallic component in an electroless composite plating solution, comprising:

measuring transmissivity or absorbance of at least two different wavelengths as measured values of said electroless composite plating solution disposed in an absorbance cell, wherein said at least two different wavelengths includes a first wavelength and a second wavelength in the condition that the concentration of said metallic component in said electroless composite plating solution is fixed, and the concentration of a composite material in said electroless composite plating solution is varied;

obtaining the following relational equation from the relationship between the absorbance ($A_1$) at said first wavelength and the absorbance ($A_2$) at said second wavelength, wherein $A_1$ is greater than $A_2$, $y = \alpha x + \beta$, where x is the absorbance at the second wavelength, y is the absorbance at the first wavelength, and $\alpha$ and $\beta$ are coefficients;

measuring transmissivities or absorbances at said first wavelength and said second wavelength in the condition that the concentration of said metallic component in said electroless composite plating solution is varied, and said concentration of said composite material in said electroless composite plating solution is varied;

obtaining the following relational equation from the relationship between a $\kappa$ value and said concentration of said metallic component, $M = \gamma\kappa - \delta$, where M is the concentration of said metallic component in said electroless composite plating solution, $\kappa$ is the absorbance at said first wavelength minus the product of $\alpha$, obtained in the first equation, multiplied by the absorbance at said second wavelength, and $\gamma$, $\delta$ are coefficients; and measuring said absorbances at said first and second wavelengths to obtain the concentration of said metallic ion from said relational equation $M = \gamma\kappa - \delta$.

2. An automatic analysis and control method according to claim 1 wherein said measuring transmissivity or absorbance comprises spectrometrically conditioning at least one of the at least two different wavelengths so that a half-width is 1 to not more than 100 nm.

3. An automatic analysis and control method according to claim 1 wherein said measuring transmissivity or absorbance comprises obtaining the different wavelengths by selecting at least one measurement wavelength in a wavelength range of 250 to 350 nm or 450 to 550 nm, and selecting at least another measurement wavelength not overlapping with said at least one measurement wavelength in a wavelength range of 350 to 450 nm or 550 to 800 nm.

4. An automatic analysis and control method according to claim 1, wherein said measuring transmissivity or absorbance comprises setting a measuring time table so that a standing time of not less than 15 sec is secured after an introduction of said electroless composite plating solution into said absorbance cell and before a start of measurement of the transmissivity or the absorbance.

5. An automatic analysis and control method according to claim 1, further comprising periodically introducing pure water into said absorbance cell to wash said absorbance cell and measuring the transmissivity or the absorbance at a set measurement wavelength in a condition where said absorbance cell is filled with pure water, and the thus measured value is used as a reference value of 100% transmissivity or absorbance relative to the measured values of transmissivity or absorbance of said electroless composite plating solution measured in a period before the next similar measurement for pure water.

6. An automatic analysis and control method according to claim 1, further comprising:

providing a sampling pipe extending to said absorption cell, providing a vertically elongated plating solution dwell portion having a cross sectional area of not less than two times of the cross sectional area of said sampling pipe and having an inlet at an upper portion of said plating solution dwell portion for feeding said electroless composite plating solution into said plating solution dwell portion, and an outlet at a lower portion of said plating solution dwell portion, and preventing fine bubbles in said electroless composite plating solution from being fed upstream into said absorbance cell.

7. An automatic analysis and control method according to claim 1, wherein said electroless composite plating solution is an electroless composite nickel plating solution, and a nickel component in said electroless composite nickel plating solution is measured.

* * * * *